(12) United States Patent  
Manchand et al.

(10) Patent No.: US 6,492,353 B1
(45) Date of Patent: Dec. 10, 2002

(54) 1,3-DIHYDROXY-20,20-CYCLOALKYL-VITAMIN $D_3$ ANALOGS

(75) Inventors: Percy Sarwood Manchand, Montclair, NJ (US); Milan Radoje Uskokovic, Upper Montclair, NJ (US)

(73) Assignees: Syntex LLC, Palo Alto, CA (US); Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/148,018

(22) Filed: Sep. 3, 1998

Related U.S. Application Data

(60) Provisional application No. 60/058,132, filed on Sep. 8, 1997.

(51) Int. Cl.[7] .............................................. C07C 401/01
(52) U.S. Cl. ....................................... 514/167; 552/653
(58) Field of Search ........................... 552/653; 514/167

(56) References Cited

U.S. PATENT DOCUMENTS

| | | | | |
|---|---|---|---|---|
| 4,804,502 A | | 2/1989 | Baggiolini et al. | 260/397.2 |
| 4,851,401 A | * | 7/1989 | DeLuca et al. | 514/167 |
| 5,087,619 A | * | 2/1992 | Baggiolini et al. | 514/167 |
| 5,403,940 A | | 4/1995 | Valles et al. | 549/300 |
| 5,428,029 A | | 6/1995 | Doran et al. | 514/167 |
| 5,446,035 A | | 8/1995 | Neef et al. | 514/167 |
| 5,447,924 A | * | 9/1995 | Bretting | 514/167 |
| 5,583,125 A | | 12/1996 | Steinmeyer et al. | 514/167 |
| 5,585,368 A | | 12/1996 | Steinmeyer et al. | 514/167 |
| 5,585,369 A | * | 12/1996 | DeLuca et al. | 514/167 |
| 5,637,742 A | | 6/1997 | Valles et al. | 552/653 |
| 6,121,312 A | * | 9/2000 | Reddy | 514/451 |

FOREIGN PATENT DOCUMENTS

| | | | |
|---|---|---|---|
| EP | 0 580 968 A2 | | 2/1994 |
| EP | 0808831 | * | 11/1997 |
| WO | WO 89/10351 A1 | | 11/1989 |
| WO | WO 95/01960 A1 | | 1/1995 |

OTHER PUBLICATIONS

Wagen Ole Godtfredsen (CA 119:125211, abstract of GB 2260904), 1992.*

Danielsson, et al., *J. Cellular Biochemistry*, vol. 63 (1996), pp 199–206, "Potent Gene Regulatory and Antiproliferative Activities of 20–Methyl Analogues of 1,25 Dihydroxyvitamin D3".

* cited by examiner

*Primary Examiner*—Sabiha Qazi
(74) *Attorney, Agent, or Firm*—Rohan Peries

(57) ABSTRACT

This invention relates to 1,3-dihydroxy-20,20-dialkyl-vitamin $D_3$ analogs of Formula (I):

(I):

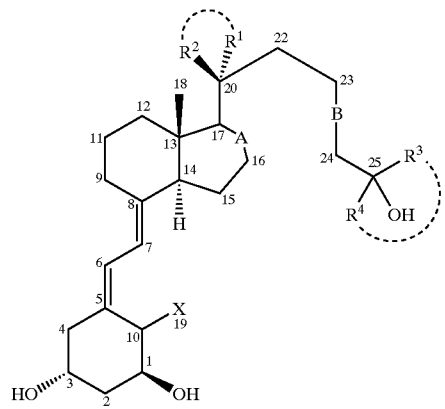

compositions comprising the analogs, methods of preparing the analogs and methods of treatment of osteoporosis, secondary hyperparathyroidism, cancer and autoimmune diseases using such analogs.

30 Claims, No Drawings

1,3-DIHYDROXY-20,20-CYCLOALKYL-VITAMIN D₃ ANALOGS

CROSS-REFERENCE TO RELATED APPLICATION

This application claims the benefit under 35 U.S.C. 119(e) of U.S. provisional patent application No. 60/058,132, filed Sep. 8, 1997.

BACKGROUND OF THE INVENTION

1. Field of the Invention

This invention relates to 1,3-dihydroxy-20,20-dialkyl-vitamin $D_3$ analogs, compositions comprising the analogs and methods of treatment of osteoporosis, secondary hyperparathyroidism, cancer and autoimmune diseases using such analogs.

2. Description of Related Art a. Osteoporosis

Osteoporosis is the most common form of metabolic bone disease and may be considered the symptomatic, fracture stage of bone loss (osteopenia). Although osteoporosis may occur secondary to a number of underlying diseases, 90% of all cases appear to be idiopathic. Postmenopausal women are at risk for idiopathic osteoporosis (postmenopausal or Type I osteoporosis); another particularly high risk group for idiopathic osteoporosis is the elderly of either sex (senile or Type II osteoporosis). Osteoporosis has also been related to corticosteroid use, immobilization or extended bed rest, alcoholism, diabetes, gonadotoxic chemotherapy, hyperprolactinemia, anorexia nervosa, primary and secondary amenorrhea, transplant immunosuppression, and oophorectomy. Postmenopausal osteoporosis is characterized by fractures of the spine, while femoral neck fractures are the dominant features of senile osteoporosis.

The mechanism by which bone is lost in osteoporotics is believed to involve an imbalance in the process by which the skeleton renews itself. This process has been termed bone remodeling. It occurs in a series of discrete pockets of activity. These pockets appear spontaneously within the bone matrix on a given bone surface as a site of bone resorption. Osteoclasts (bone dissolving or resorbing cells) are responsible for the resorption of a portion of bone of generally constant dimension. This resorption process is followed by the appearance of osteoblasts (bone forming cells) which then refill with new bone the cavity left by the osteoclasts.

In a healthy adult subject, osteoblasts and osteoclasts function so that bone formation and bone resorption are in balance. However, in osteoporotics an imbalance in the bone remodeling process develops which results in bone being replaced at a slower rate than it is being lost. Although this imbalance occurs to some extent in most individuals as they age, it is much more severe and occurs at a younger age in postmenopausal osteoporotics, following oophorectomy, or in iatrogenic situations such as those resulting from corticosteroid therapy or the immunosuppression practiced in organ transplantation.

Various approaches have been suggested for increasing bone mass in humans afflicted with osteoporosis, including administration of androgens, fluoride salts, and parathyroid hormone and modified versions of parathyroid hormone. It has also been suggested that bisphosphonates, calcitonin, calcium, 1,25-dihydroxy vitamin $D_3$ and some of its analogs, and/or estrogens, alone or in combination, may be useful for preserving existing bone mass.

Vitamin $D_3$ is a critical element in the metabolism of calcium, promoting intestinal absorption of calcium and phosphorus, maintaining adequate serum levels of calcium and phosphorus, and stimulating flux of calcium into and out of bone. The D vitamins are hydroxylated in vivo, with the resulting 1α,25-dihydroxy metabolite being the active material. Animal studies with 1,25-$(OH)_2$ vitamin $D_3$ have suggested bone anabolic activity. Aerssens et al., in *Calcif Tissue Int*, 55:443–450 (1994), reported upon the effect of 1α-hydroxy vitamin $D_3$ on bone strength and composition in growing rats with and without corticosteroid treatment. However, human usage is restricted to antiresorption due to the poor therapeutic ratio (hypercalciuria and hypercalcemia as well as nephrotoxicity).

Dechant and Goa, in "Calcitriol. A review of its use in the treatment of postmenopausal osteoporosis and its potential in corticosteroid-induced osteoporosis", Drugs Aging [NEW ZEALAND 5 (4): 300–17 (1994)], reported that 1,25-dihydroxy vitamin $D_3$ (calcitriol) has shown efficacy in the treatment of postmenopausal osteoporosis (and promise in corticosteroid-induced osteoporosis) based upon a clinical trial in 622 women with postmenopausal osteoporosis. Patients with mild to moderate disease (but not those with more severe disease) who received calcitriol (0.25 microgram twice daily) had a significant 3-fold lower rate of new vertebral fractures after 3 years of treatment compared with patients receiving elemental calcium 1000 mg/day. In patients commencing long term treatment with prednisone or prednisolone, calcitriol 0.5 to 1.0 micrograms/day plus calcium 1000 mg/day, administered with or without intranasal calcitonin 400 IU/day, prevented steroid-induced bone loss. Overall, calcitriol was well tolerated. At recommended dosages hypercalcaemia was infrequent and mild, generally responding to reductions in calcium intake and/or calcitriol dosage. The narrow therapeutic window of calcitriol required that its use be adequately supervised, with periodic monitoring of serum calcium and creatinine levels. This study clearly identifies the key limitation of calcitriol therapy as the close proximity of therapeutic and toxic doses.

This invention provides novel vitamin $D_3$ derivatives which have more favorable therapeutic doses.

b. Cancer

Epidemiologic studies have correlated sun or UV light exposure with a lower incidence of a variety of malignancies, including breast, colon and prostate cancer. Evidence from receptor studies demonstrates that besides the classic target organs, such as intestine, kidney and bone, vitamin D receptors (VDR) are present on a wide variety of human normal and cancer cell lines and fresh tissue. Growth inhibition with vitamin D or 1,25-dihydroxycholecalciferol does not always translate into potential therapeutic efficacy in vivo. Early in vivo studies have focused on the antiproliferative effects of 1,25-dihydroxycholecalciferol and its analogues in murine leukemia model systems where 1,25-dihydroxycholecalciferol has been shown to induce not only an anti-proliferative effect, but also a differentiating effect. Therapeutic efficacy in vivo has its limitations due to the hypercalcemia observed with high dose treatment of the parent 1,25-dihydroxycholecalciferol. As a result, a number of analogues have been developed that produce significant anti-tumor effects without hypercalcemia.

Steinmeyer et al in U.S. Pat. No. 5,585,368 discloses 1α-25-dihydroxy-20-disubstituted vitamin $D_3$ analogs for the treatment of hyperproliferative disorders of the skin, malignant tumors such as leukemia, colon and breast cancers, autoimmune diseases such as diabetes and for the treatment of sebaceous gland diseases. Danielsson, C. et al in *J. Cell Biochem.*, 63, No. 2, 199–206 (1996) disclose 20-methyl analogues of 1,25-dihydroxy vitamin $D_3$, including 1α-25-dihydroxy-20-methyl-23(E)-ene-cholecalciferol for the treatment of hyperproliferative disorders. This invention provides novel vitamin $D_3$ derivatives for the treatment of hyperproliferative disorders of the skin, malignant tumors such as leukemia, colon and breast cancers, autoimmune diseases such as diabetes and for the treatment of sebaceous gland diseases which have more favorable therapeutic ratios or margins.

c. Hyperparathyroidism

Secondary hyperparathyroidism is routine in patients with chronic renal failure. It is established that the reduction of renal $1,25(OH)_2$ vitamin $D_3$ (calcitriol) synthesis is one of the principal mechanisms leading to the secondary hyperparathyroidism in these patients and it has been shown that calcitriol possesses direct suppressive action on PTH synthesis. Therefore, administration of calcitriol has been recommended for the treatment of secondary hyperparathyroidism in these patients. However, as described above, calcitriol has potent hypercalcemic effects giving it a narrow therapeutic window which limits its usage, especially at high doses. It would therefore be desirable to have an alternative means of treating hyperparathyroidism and repleting circulating vitamin $D_3$ activity without incurring these undesirable hypercalcemic effects.

This invention provides novel vitamin $D_3$ derivatives which have more favorable therapeutic windows.

SUMMARY OF THE INVENTION

One aspect of the invention concerns Vitamin $D_3$ analogs of the Formula (I):

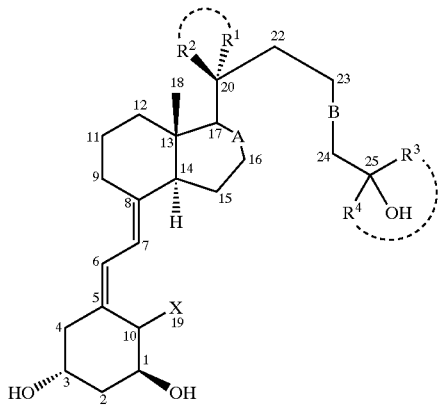

wherein:

X is hydrogen or $=CH_2$;

$R^1$ and $R^2$ are, independently of each other, a $(C_1–C_4)$ alkyl or $(C_1–C_4)$fluoroalkyl, or $R^1$ and $R^2$ together with C20 form a $(C_3–C_6)$cycloalkyl or $(C_3–C_6)$ cyclofluoroalkyl, or $R^1$ and $R^2$ together form $=CH_2$;

$R^3$ and $R^4$ are, independently of each other, a $(C_1–C_4)$ alkyl or $(C_1–C_4)$fluoroalkyl, or $R^3$ and $R^4$ together with C25 form a $(C_3–C_9)$cycloalkyl or $(C_3–C_9)$ cyclofluoroalkyl;

A is a single or a double bond; and

B is a single, double or triple bond;

and prodrugs thereof, provided that:
(i) when $R^1$ and $R^2$ are $(C_1–C_4)$alkyl or $R^1$ and $R^2$ together with C20 form a cyclopropyl group or $=CH_2$, $R^3$ and $R^4$ are $(C_1–C_4)$alkyl, trifluoromethyl or $R^3$ and $R^4$ together with C25 form $(C_3–C_6)$ cycloalkyl and A is a single bond, then B is not a trans double bond;
(ii) when B is a single bond, then $R^1$ and $R^2$ together with C20 form a $(C_3–C_6)$cycloalkyl or $(C_3–C_6)$ cyclofluoroalkyl group; and
(iii) when $R^1$ and $R^2$ are $(C_1–C_4)$alkyl, $R^3$ and $R^4$ are $(C_1–C_4)$alkyl, $X=CH_2$ and A is a single bond, then B is not a double bond.

A second aspect of this invention relates to a method for treating osteoporosis or secondary hyperparathyroidism via administration of a compound of Formula (I), wherein:

X is hydrogen or $=CH_2$;

$R^1$ and $R^2$ are, independently of each other, a $(C_1–C_4)$ alkyl or $(C_1–C_4)$fluoroalkyl, or $R^1$ and $R^2$ together with C20 form a $(C_3–C_6)$cycloalkyl or $(C_3–C_6)$ cyclofluoroalkyl, or $R^1$ and $R^2$ together form $=CH_2$;

$R^3$ and $R^4$ are, independently of each other, a $(C_1–C_4)$ alkyl or $(C_1–C_4)$fluoroalkyl, or $R^3$ and $R^4$ together with C25 form a $(C_3–C_9)$cycloalkyl or $(C_3–C_9)$ cyclofluoroalkyl;

A is a single or a double bond; and

B is a single, double or triple bond;

and prodrugs thereof, in an amount therapeutically effective to restore bone density to an asymptomatic level, without inducing hypercalciuria, hypercalcemia, or nephrotoxicity.

A third aspect of this invention relates to a method for treating cancer via administration of a compound of Formula (I), wherein:

X is hydrogen or $=CH_2$;

$R^1$ and $R^2$ are, independently of each other, a $(C_1–C_4)$ alkyl or $(C_1–C_4)$fluoroalkyl, or $R^1$ and $R^2$ together with C20 form a $(C_3–C_6)$cycloalkyl or $(C_3–C_6)$ cyclofluoroalkyl, or $R^1$ and $R^2$ together form $=CH_2$;

$R^3$ and $R^4$ are, independently of each other, a $(C_1–C_4)$ alkyl or $(C_1–C_4)$fluoroalkyl, or $R^3$ and $R^4$ together with C25 form a $(C_3–C_9)$cycloalkyl or $(C_3–C_9)$ cyclofluoroalkyl;

A is a single or a double bond; and

B is a single, double or triple bond;

and prodrugs thereof, in an amount therapeutically effective, without inducing hypercalciuria, hypercalcemia, or nephrotoxicity provided that:
(i) when $R^1$ and $R^2$ are $(C_1–C_4)$alkyl or $R^1$ and $R^2$ together with C20 form a cyclopropyl group or $=CH_2$, $R^3$ and $R^4$ are $(C_1–C_4)$alkyl, trifluoromethyl or $R^3$ and $R^4$ together with C25 form $(C_3–C_6)$ cycloalkyl and A is a single bond, then B is not a trans double bond;
(ii) when B is a single bond, then $R^1$ and $R^2$ together with C20 form a $(C_3–C_6)$cycloalkyl or $(C_3–C_6)$ cyclofluoroalkyl group; and
(iii) when $R^1$ and $R^2$ are $(C_1–C_4)$alkyl, $R^3$ and $R^4$ are $(C_1–C_4)$alkyl, $X=CH_2$ and A is a single bond, then B is not a double bond.

A fourth aspect of this invention relates to pharmaceutical compositions comprising a pharmaceutically acceptable carrier and a vitamin $D_3$ analog of Formula (I).

DETAILED DESCRIPTION OF THE INVENTION

The vitamin $D_3$ analogs of the present invention have the following general structure:

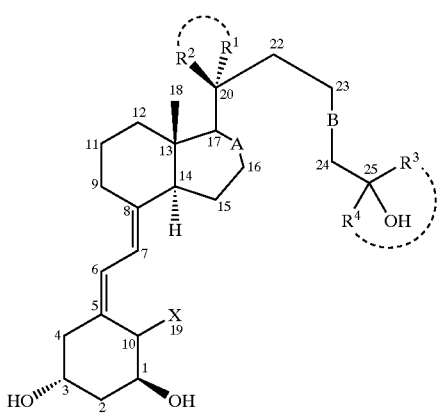

wherein:

X is hydrogen or =CH$_2$;

R$^1$ and R$^2$ are, independently of each other, a (C$_1$–C$_4$) alkyl or (C$_1$–C$_4$)fluoroalkyl, or R$^1$ and R$^2$ together with C20 form a (C$_3$–C$_6$)cycloalkyl or (C$_3$–C$_6$) cyclofluoroalkyl, or R$^1$ and R$^2$ together form =CH$_2$;

R$^3$ and R$^4$ are, independently of each other, a (C$_1$–C$_4$) alkyl or (C$_1$–C$_4$)fluoroalkyl, or R$^3$ and R$^4$ together with C25 form a (C$_3$–C$_9$)cycloalkyl or (C$_3$–C$_9$) cyclofluoroalkyl;

A is a single or a double bond; and

B is a single, double or triple bond;

and prodrugs thereof, provided that:

(i) when R$^1$ and R$^2$ are (C$_1$–C$_4$)alkyl or R$^1$ and R$^2$ together with C20 form a cyclopropyl group or =CH$_2$, R$^3$ and R$^4$ are (C$_1$–C$_4$)alkyl, trifluoromethyl or R$^3$ and R$^4$ together with C25 form (C$_3$–C$_6$) cycloalkyl and A is a single bond, then B is not a trans double bond;

(ii) when B is a single bond, then R$^1$ and R$^2$ together with C20 form a (C$_3$–C$_6$)cycloalkyl or (C$_3$–C$_6$) cyclofluoroalkyl group; and (iii) when R$^1$ and R$^2$ are (C$_1$–C$_4$)alkyl, R$^3$ and R$^4$ are (C$_1$–C$_4$)alkyl, X=CH$_2$ and A is a single bond, then B is not a double bond.

A method for treating osteoporosis or secondary hyperparathyroidism via administration of a compound of Formula (I), wherein:

X is hydrogen or =CH$_2$;

R$^1$ and R$^2$ are, independently of each other, a (C$_1$–C$_4$) alkyl or (C$_1$–C$_4$)fluoroalkyl, or R$^1$ and R$^2$ together with C20 form a (C$_3$–C$_6$)cycloalkyl or (C$_3$–C$_6$) cyclofluoroalkyl, or R$^1$ and R$^2$ together form =CH$_2$;

R$^3$ and R$^4$ are, independently of each other, a (C$_1$–C$_4$) alkyl or (C$_1$–C$_4$)fluoroalkyl, or R$^3$ and R$^4$ together with C25 form a (C$_3$–C$_9$)cycloalkyl or (C$_3$–C$_9$) cyclofluoroalkyl;

A is a single or a double bond; and

B is a single, double or triple bond;

and prodrugs thereof, in an amount therapeutically effective to restore bone density to an asymptomatic level, without inducing hypercalciuria, hypercalcemia, or nephrotoxicity.

A method for treating cancer via administration of a compound of Formula (I), wherein:

X is hydrogen or =CH$_2$;

R$^1$ and R$^2$ are, independently of each other, a (C$_1$–C$_4$) alkyl or (C$_1$–C$_4$)fluoroalkyl, or R$^1$ and R$^2$ together with C20 form a (C$_3$–C$_6$)cycloalkyl or (C$_3$–C$_6$) cyclofluoroalkyl, or R$^1$ and R$^2$ together form =CH$_2$;

R$^3$ and R$^4$ are, independently of each other, a (C$_1$–C$_4$) alkyl or (C$_1$–C$_4$)fluoroalkyl, or R$^3$ and R$^4$ together with C25 form a (C$_3$–C$_9$)cycloalkyl or (C$_3$–C$_9$) cyclofluoroalkyl;

A is a single or a double bond; and

B is a single, double or triple bond;

and prodrugs thereof, in an amount therapeutically effective, without inducing hypercalciuria, hypercalcernia, or nephrotoxicity, provided that:

(i) when R$^1$ and R$^2$ are (C$_1$–C$_4$)alkyl or R$^1$ and R$^2$ together with C20 form a cyclopropyl group or =CH$_2$, R$^3$ and R$^4$ are (C$_1$–C$_4$)alkyl, trifluoromethyl or R$^3$ and R$^4$ together with C25 form (C$_3$–C$_6$) cycloalkyl and A is a single bond, then B is not a trans double bond;

(ii) when B is a single bond, then R$^1$ and R$^2$ together with C20 form a (C$_3$–C$_6$)cycloalkyl or (C$_3$–C$_6$) cyclofluoroalkyl group; and (iii) when R$^1$ and R$^2$ are (C$_1$–C$_4$)alkyl, R$^3$ and R$^4$ are (C$_1$–C$_4$)alkyl, X=CH$_2$ and A is a single bond, then B is not a double bond.

Definitions

As used herein, the term (C$_1$–C$_4$) alkyl means a fully-saturated hydrocarbon radical having one to four carbon atoms; a (C$_1$–C$_4$) fluoroalkyl is an alkyl radical, as defined above, in which one or more hydrogen atoms attached to the carbon backbone have been substituted with one or more fluorine atoms. A (C$_3$–C$_6$) cycloalkyl is a cyclic saturated hydrocarbon radical having three to six ring carbon atoms; a (C$_3$–C$_6$) cyclofluoroalkyl is a cycloalkyl radical, as defined above, in which one or more hydrogen atoms attached to the carbon backbone have been substituted with one or more fluorine atoms. A (C$_3$–C$_9$) cycloalkyl is a cyclic saturated hydrocarbon radical having three to nine ring carbon atoms; a (C$_3$–C$_9$) cyclofluoroalkyl is a cyclic saturated hydrocarbon radical having three to nine carbon atoms in which one or more hydrogen atoms attached to the carbon backbone have been substituted with one or more fluorine atoms.

Further as used herein, by double bond it is meant an unsaturated linkage between two adjacent carbon atoms in which two pairs of electrons are shared equally, and wherein each carbon atom bears two single-bonded substituents in either a cis (Z) or a trans (E) configuration about the double bond.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy group in compound (I) is bonded to any group that may be cleaved i vivo to regenerate the free hydroxyl group. Examples of prodrugs include, but are not limited to esters (e.g., acetate, formate, and benzoate derivatives), carbamates (e.g., N,N-dimethylaminocarbonyl) and ethers of hydroxy functional groups in compounds of Formula (I), and the like. Such compounds are routinely made by one of skill in the art by acylating or etherifying the hydroxy group in the parent molecule.

A "therapeutically effective amount" means the amount of a compound that, when administered to a mammal for treating or preventing a disease, is sufficient to effect such treatment or prevention for the disease. The "therapeutically effective amount" will vary depending on the compound, the disease and its severity and the age, weight, etc., of the mammal to be treated.

The compounds of the present invention may be generically described as 1α,25-dihydroxy-20,20-dialkyl and 1α,25-dihydroxy-20,20-dialkyl-19-nor analogs of vitamin $D_3$.

Nomenclature

The compounds of the invention are named using the numbering system shown in FIG. (1) below.

FIG. (1)

For example, a compound of the invention where X is =$CH_2$, $R^1$ and $R^2$ together form a cyclopropyl group, A is a single bond and B is a triple bond is named as 1α-25-dihydroxy-23-yne-20,21,28-cyclopropyl-cholecalciferol.

The following Table I provides some representative examples of compounds of the present invention:

TABLE I

| CPD # | A | B | $R^1$ | $R^2$ | $R^3$ | $R^4$ | X |
|---|---|---|---|---|---|---|---|
| 1 | — | ≡ | —$CH_2CH_2$— | | $CH_3$ | $CH_3$ | =$CH_2$ |
| 2 | — | ≡ | —$CH_2CH_2$— | | $CH_3$ | $CH_3$ | $H_2$ |
| 3 | — | ≡ | —$CH_2CH_2$— | | $CF_3$ | $CF_3$ | =$CH_2$ |
| 4 | — | ≡ | —$CH_2CH_2$— | | $CF_3$ | $CF_3$ | $H_2$ |
| 5 | — | cis=bond | —$CH_2CH_2$— | | $CF_3$ | $CF_3$ | =$CH_2$ |
| 6 | — | cis=bond | —$CH_2CH_2$— | | $CF_3$ | $CF_3$ | $H_2$ | and are named as:
1. 1,25-dihydroxy-23-yne-20,21,28-cyclopropyl-cholecalciferol.
2. 1,25-dihydroxy-23-yne-20,21,28-cyclopropyl-19-nor-cholecalciferol.
3. 1,25-dihydroxy-23-yne-26,27-hexafluoro-20,21,28-cyclopropyl-cholecalciferol.
4. 1,25-dihydroxy-23-yne-26,27-hexafluoro-20,21,28-cyclopropyl-19-norcholecalciferol.
5. 1,25-dihydroxy-23-(Z)-ene-26,27-hexafluoro-20,21,28-cyclopropyl-cholecalciferol.
6. 1,25-dihydroxy-23-(Z)-ene-26,27-hexafluoro-20,21,28-cyclopropyl-19-norcholecalciferol.

Preferred Embodiments

While the broadest definition of this invention is set forth in the Summary of the Invention, certain compounds of Formula (I) are preferred.

A preferred group of compounds are those wherein:

A is a single or a double bond, preferably a single bond; and

B is a triple bond.

Another preferred group of compounds are those wherein:

A is a double bond; and

B is a double bond.

Yet another preferred group of compounds are those wherein:

A is a single or a double bond, preferably a single bond; and

B is a cis double bond.

Within these preferred groups of compounds, more preferred groups are those wherein:

$R^1$ and $R^2$ together with C20 form a ($C_3$–$C_6$)cycloalkyl, preferably a cyclopropyl; and $R^3$ and $R^4$ are, independently of each other, a ($C_1$–$C_4$) alkyl or a ($C_1$–$C_4$)fluoroalkyl, preferably methyl, ethyl, trifluoromethyl, 1,1-difluoroethyl or 2,2,2-trifluoroethyl, more preferably methyl or trifluoromethyl.

General Synthesis

Analogs of this invention may generally be prepared by reaction and combination of fragments of Vitamin $D_3$ molecules (see e.g., Shiuey et al., *J. Org. Chem*, 55:243 (1990); Wovkulich, P. M. et al., *Tetrahedron*, 40, 2283 (1984); Baggiolini E. B. et al *J. Org. Chem.*, 51, 3098–3108, (1986) and Steinmeyer et al., U.S. Pat. No. 5,585,368.

The starting materials and reagents used in preparing these compounds are either available from commercial suppliers such as Aldrich Chemical Co., (Milwaukee, Wis.), or Sigma (St. Louis, Mo.) or they can be prepared by methods known to those skilled in the art following procedures set forth in references such as Fieser and Fieser's *Reagents for Organic Synthesis*, Vol. 1–15 (John Wiley and Sons, 1991); March's *Advanced Organic Chemistry*, (John Wiley and Sons 4th Edition) and Larock's *Comprehensive Organic Transformations* (VCH Publishers Inc., 1989).

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

The preparation of compounds of Formula (I) and the intermediates used in their preparation is illustrated by the reaction schemes below.

Preparation of Compounds of Formula (I)

In general, a compound of Formula (I) is prepared by coupling a 4H-inden-4-one derivative of Formula (II) where $R^1$, $R^2$, $R^3$, $R^4$, A and B are as described in the Summary of the Invention and $R^5$ is hydrogen or a hydroxy protecting group (e.g., trialkylsilyl, preferably trimethylsilyl) with a diphenylphosphine oxide derivative of a compound of Formula (III) where X is hydrogen or =$CH_2$, as shown in Scheme I below.

Scheme I

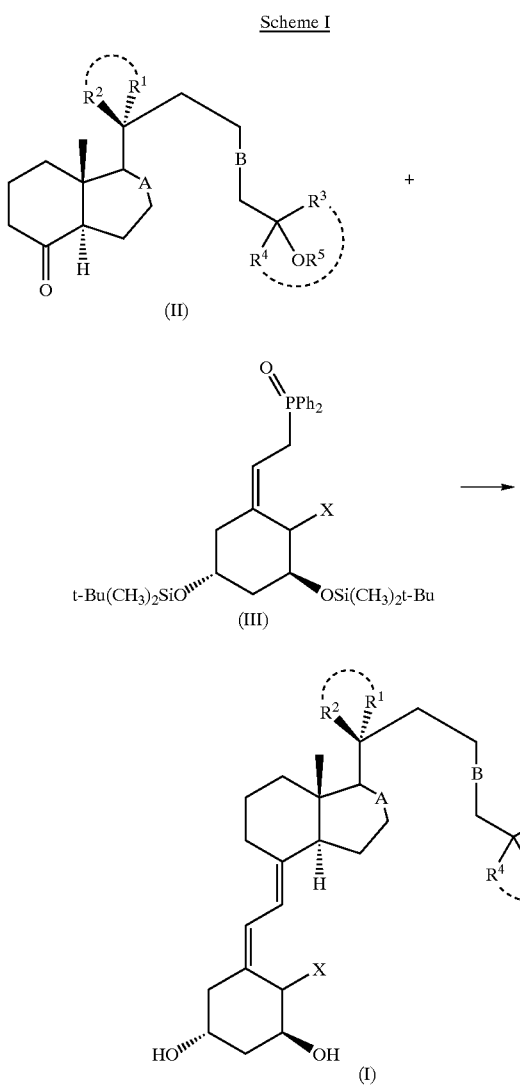

The coupling reaction is carried out in the presence of a strong base such as an alkyllithium like n-butyllithium in a mixture of hexane and tetrahydrofuran at −78° C. to give a trisily derivative of compound of Formula (I). Removal of the sily protecting groups with tetrabutylammnonium fluoride in a suitable polar organic solvent such as tetrahydrofuran provides a compound of Formula (I).

It should be noted that although the shown intermediates have hydroxy groups typically protected as silylethers, the scope of the invention includes the use of alternative hydroxyl protecting groups known in the art as described in T. W. Greene, "Protective Groups in Organic Synthesis," Wiley, New York (1991) and J. F. McOmie, "Protective Groups in Organic Chemistry," Plenum Press, London (1973), together with alternative methods for deprotection.

Synthesis of compounds of Formula (III) are known and conventional in this art. See, for example, U.S. Pat. No. , 5,585,368 to Steinmeyer et al., U.S. Pat. No. 5,384,314 to Doran et al., U.S. Pat. No. 5,428,029 to Doran et al., U.S. Pat. No. 5,451,574 to Baggiolini et al.; pending U.S. patent application Ser. No. 60/018,219; Shiuey et al., *J. Org. Chem.*, 55:243–247 (1990), Kiegel, J. et al. and *Tetr. Lett.*, 32:6057–6060 (1991), Perlman, K. L., et al., *Tetr. Lett.*, 32:7663–7666 (1991).

Synthesis of compounds of Formula (II) is described in Scheme II below.

Detailed descriptions of the synthesis of compounds of Formula (I) where $R^1$ and $R^2$ together form a cyclopropyl ring, X is =CH$_2$ or H$_2$, A is a single bond, B is a triple bond and $R^3$ and $R^4$ are either methyl or trifluoromethyl are described in Examples 2, 3, 5 and 6.

Detailed descriptions of the synthesis of compounds of Formula (I) where $R^1$ and $R^2$ together form a cyclopropyl ring, X is =CH$_2$ or H$_2$, A is a single bond, B is a cis double bond and $R^3$ and $R^4$ are trifluoromethyl are described in Examples 8 and 9.

Preparation of Compounds of Formula (II)

The 4H-inden-4-one derivatives of Formula (II) are prepared as shown in Scheme II below.

Scheme II

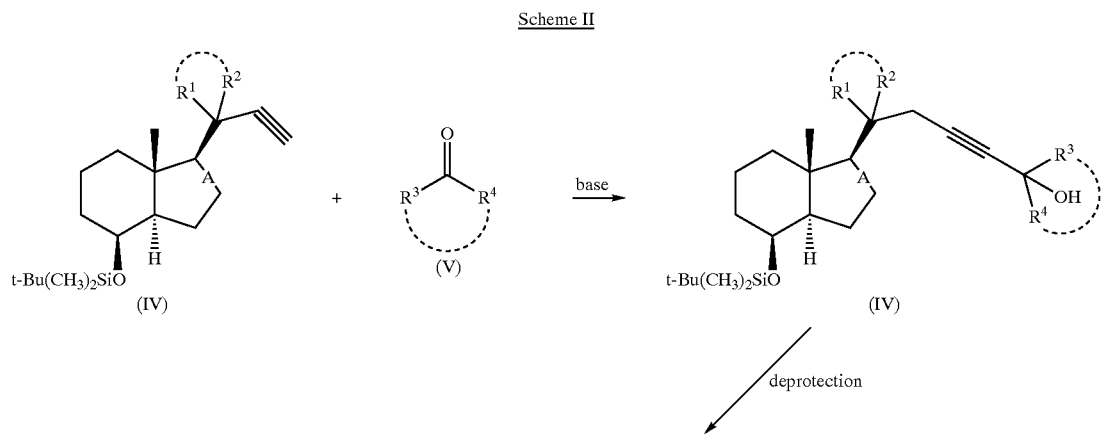

-continued

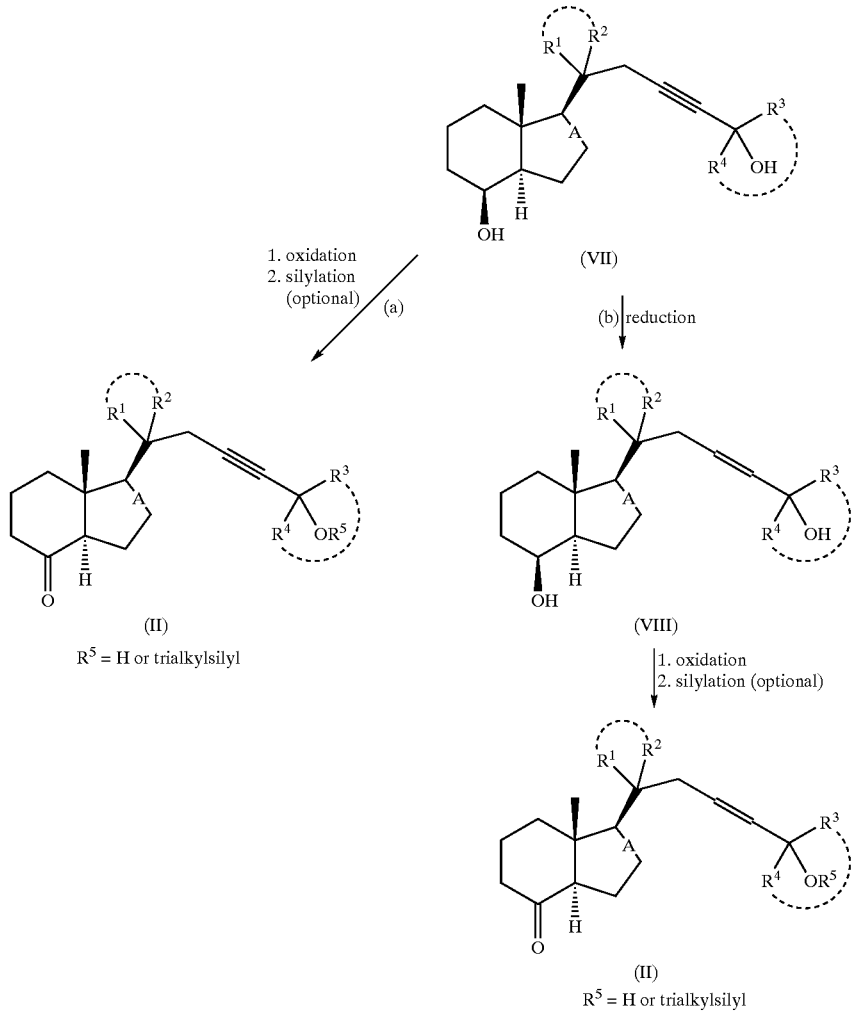

As shown above, preparation of a compound of Formula (II) involves preparation of a common intermediate, 1-[(5-hydroxy)-3-alkynyl]-inden-4-ol derivative (VII), which is then converted to a compound of Formula (II) where B is either a double or a triple bond by following method (a) or method (b) respectively.

Compound (VII) is prepared by condensation of lithium acetylide derived from a 1-(3-alkynyl)-4-tert-butyldimethylsilyloxy-7a-methyl-indene derivative (IV) with a ketone of Formula (V) where $R^3$ and $R^4$ are as defined in the Summary of the Invention to give a 1-[(5-hydroxy)-3-alkynyl]-4-tert-butyldimethysilyloxy-7a-methyl-indene derivative (VI). The condensation reaction is carried out in the presence of a strong base such as n-butyllithium in an aprotic organic solvent such as tetrahydrofuran and at low temperatures ranging between −50 to −100° C. Removal of the silyl group with tetrabutylammonium fluoride in an suitable organic solvent such as tetrahydrofuran gives the 1-[(5-hydroxy)-3-alkynyl]-inden-4-ol derivative (VII).

A detailed description of the synthesis of compounds of Formula (IV) where $R^1$ and $R^2$ together form a cyclopropyl ring and A is a single bond is given in Example 1. Synthesis of other compounds of Formula (IV) and alternative methods for preparing compounds of Formula (VII) have been described in copending U.S. application Ser. No. 08/857,569, published as EP 0 808,832 A2, whose disclosure is hereby incorporated by reference.

A compound of Formula (II) where B is a triple bond and $R^5$ is hydrogen is prepared, as shown in method (a), by oxidation of the hydroxy group at the 4-position in compound (VII) to the keto group with a suitable oxidizing agent such as pyridinium dichromate at room temperature. The oxidation reaction is carried out in a chlorinated hydrocarbon solvent such as methylene chloride, chloroform and the like. A compound of Formula (II) where $R^5$ is hydrogen is converted to the corresponding compound of Formula (II) where $R^5$ is trialkylsilyl, preferably trimethylsilyl, by reacting it with a suitable silylating agent such as 1-trimethylsilylimidazole in a non-alcoholic organic solvent such as tetrahydrofuran, methylene chloride, preferably methylene chloride, and the like.

Synthesis of compounds of Formula (II) where A is a single bond, B is a triple bond, $R^1$ and $R^2$ together form a cyclopropyl ring, $R^1$ is trimethylsilyl or hydrogen and $R^3$ and $R^4$ are methyl or trifluoromethyl are described in Examples 1 and 4.

Alternatively, a compound of Formula (II) where B is a double bond is prepared, as shown in method (b), by partial reduction of the triple bond in compound (VII) with a suitable reducing agent to give a 3-alkene-4H-inden-4-ol of Formula (VIII). The choice of the reducing agent depends on the configuration about the double bond. If the E configuration is desired, then the reduction is carried out with lithium aluminum hydride in the presence of an alkali metal alkoxide, such as sodium methoxide, and in an aprotic organic solvent like ether or more preferably tetrahydrofuran. If the Z configuration is desired, then the reduction is carried out with Lindlar's catalyst. Compound (VIII) is then converted to a compound of Formula (II) where B is a double bond and $R^5$ is hydrogen or a silyl group by carrying out the oxidation and silylation steps as described above. Synthesis of a compound of Formula (II) where A is a single bond, B is a cis double bond, $R^1$ and $R^2$ together form a cyclopropyl ring, $R^5$ is trimethylsilyl and $R^3$ and $R^4$ are trifluoromethyl is described in Example 7.

A reaction scheme showing the preparation of a compound of Formula (I) where A is a single bond, B is a single bond, $R^1$ and $R^2$ form a cyclopropyl ring and X is $=CH_2$ is shown below in Scheme III and is described further in Example 10.

Scheme III

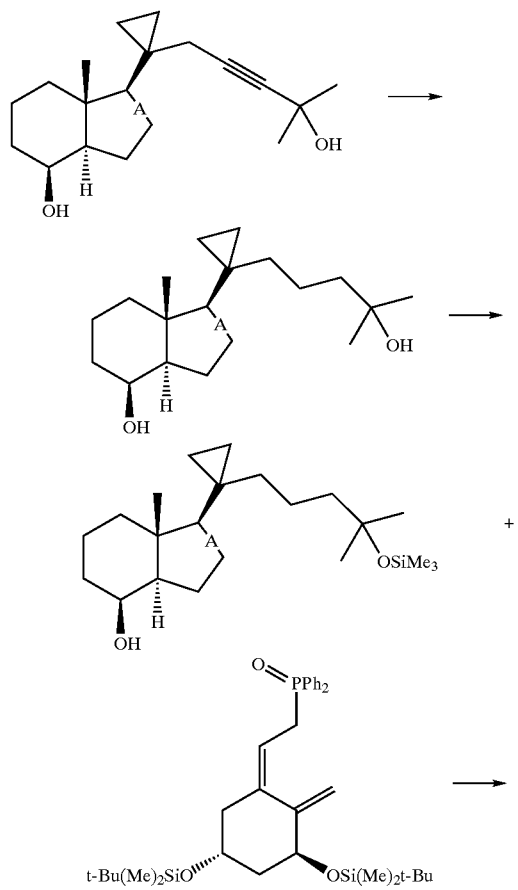

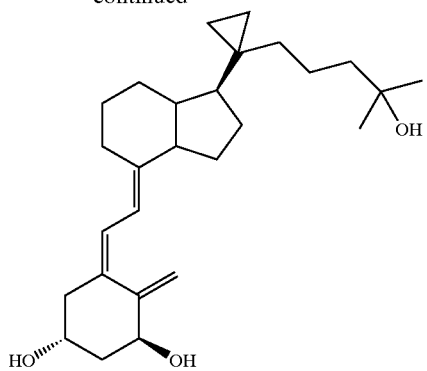

The starting material is reduced, preferably by catalytic hydrogenation, to give the completely saturated side chain derivative which is then oxidized to give the corresponding ketone. Condensation with a diphenylphosphine oxide as previously described in Scheme I followed by removal of the silyl protecting groups gives the desired compound. One of skill in the art will recognize that similar procedures may be used to form other compounds of the invention where $R^1$–$R^4$ and X may vary as described in the Summary of the Invention.

Utility

The compounds of this invention are useful for the prevention and treatment of a variety of mammalian conditions manifested by loss of bone mass. In particular, the compounds of this invention are anabolic agents and are indicated for the prophylaxis and therapeutic treatment of osteoporosis and osteopenia in mammals without inducing hypercalciuria, hypercalcemia, or nephrotoxicity. As used herein, "hypercalciuria" is excessive calcium in the urine, in humans corresponding to an excretion of greater than about 4 mg/kg/day. This often results in nephrolithiasis (renal calculi). "Hypercalcemia" is an excessive concentration of calcium in the serum; in humans (and rats) this corresponds to greater than about 10.5 mg/dl. "Intolerable hypercalcemia", usually occurring at serum calcium concentrations greater than about 12 mg/dl, is associated with emotional lability, confusion, delirium, psychosis, stupor, and coma.

The compounds of this invention are expected to be useful in the treatment of Type I (postmenopausal), Type II (senile), and Type III (iatrogenic) osteoporosis, including that associated with immunosuppressive drugs used in organ transplantation, as well in the treatment of osteodystrophy due to renal dialysis and secondary hyperparathyroidism.

Compounds of this invention are also useful in treating diseases caused by elevated levels of parathyroid hormone. In one aspect, compounds of the invention are used in treating secondary hyperparathyroidism associated with renal failure and in particular with reversing or reducing the bone loss associated with renal insufficiency. Other aspects include the treatment of renal osteodystrophy associated with late stage secondary hyperparathyroidism. Other aspects include the treatment of primary hyperparathyroidism.

Compounds of Formula (I) are also useful in treating neoplastic diseases such as leukemia, colon cancer, breast cancer and prostate cancer.

Compounds of Formula (I) are also useful in treating immunosuppressive and autoimmune diseases. Such diseases include, but are not limited to, multiple sclerosis, systemic lupus erythematosus, diabetes, thyroiditis and allograft rejection. In particular, compounds of Formula (I) are useful to treat diseases via modulation of the activity of the vitamin $D_3$ receptor (VDR). The utility of these compounds is demonstrated in vivo using murine models for these diseases as is well known in the art. See, e.g., Lemire et al., *Autoimmunity*, 12:143–148 (1992); Lemireet. al., *J. Clin. Invest.*, 87:1103–1107 (1991), Lemire et al., *Endocrinology*, 135:2818 (1994), and Lemire et al., *J. Cellular Biochem.*, 49:26–31 (1992).

Testing

The bone anabolic activity of the compounds of the invention was demonstrated in vivo in the ovariectomized rat model as described in detail in Example 10. The anti-cell proliferation activity of the compounds of the invention was demonstrated in vitro as described in detail in Examples 11 and 12. The parathyroid hormone suppressive activity of the compounds of the invention was demonstrated in vivo as described in detail in Example 13.

Administration & Pharmaceutical Compositions

In general, the compound of this invention may be administered in amounts between about 0.0002 and 5 μg per day, preferably from about 0.001 to about 2 μg per day, most preferably from about 0.002 to about 1 μg per day. For a 50 μg human subject, the daily dose of active ingredient may be from about 0.01 to about 250 μg, preferably from about 0.05 to about 100 μg, most preferably from about 0.1 to about 50 μg per day. In other mammals, such as horses, dogs, and cattle, other doses may be required. This dosage may be delivered in a conventional pharmaceutical composition by a single administration, by multiple applications, or via controlled release, as needed to achieve the most effective results, preferably once or twice daily by mouth. In certain situations, alternate day dosing may prove adequate to achieve the desired therapeutic response.

The selection of the exact dose and composition and the most appropriate delivery regimen will be influenced by, inter alia, the pharmacological properties of the formulation, the nature and severity of the condition being treated, and the physical condition and mental acuity of the recipient. In the treatment of corticosteroid induced osteopenia, it is expected that the requisite dose will be greater for higher doses of corticosteroids.

Representative delivery regimens include oral, parenteral (including subcutaneous, intramuscular and intravenous), rectal, buccal (including sublingual), pulmonary, transdermal, and intranasal, most preferably oral.

A further aspect of the present invention relates to pharmaceutical compositions comprising as an active ingredient a compound of the present invention, in admixture with a pharmaceutically acceptable, non-toxic carrier. As mentioned above, such compositions may be prepared for parenteral (subcutaneous, intramuscular or intravenous) administration, particularly in the form of liquid solutions or suspensions; for oral or buccal administration, particularly in the form of tablets or capsules; for pulmonary or intranasal administration, particularly in the form of powders, nasal drops or aerosols; and for rectal or transdermal administration.

The compositions may conveniently be administered in unit dosage form and may be prepared by any of the methods well-known in the pharmaceutical art, for example as described in *Remington's Pharmaceutical Sciences*, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Orally administrable compositions may comprise one or more physiologically compatible carriers and/or excipients and may be in solid or liquid form, including, for example, tablets, coated tablets, capsules, lozenges, aqueous or oily suspensions, solutions, emulsions, elixirs, and powders suitable for reconstitution with water or another suitable liquid vehicle before use. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethylcellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Preferred solid oral dosage forms include tablets, two-piece hard shell capsules and soft elastic gelatin (SEG) capsules. SEG capsules are of particular interest because they provide distinct advantages over the other two forms (see Seager, H., "Soft gelatin capsules: a solution to many tableting problems"; *Pharmaceutical Technology*, 9, (1985). Some of the advantages of using SEG capsules are: a) dose-content uniformity is optimized in SEG capsules because the drug is dissolved or dispersed in a liquid that can be dosed into the capsules accurately, b) drugs formulated as SEG capsules show good bioavailability because the drug is dissolved, solubilized or dispersed in an aqueous-miscible or oily liquid and therefore when released in the body produce drug dispersions of high surface area and c) degradation of drugs that are sensitive to oxidation during long-term storage is prevented because the dry shell of soft gelatin provides a barrier against the diffusion of oxygen.

The dry shell formulation typically comprises of about 40% to 60% concentration of gelatin, about a 20% to 30% concentration of plasticizer (such as glycerin, sorbitol or propylene glycol) and about a 30 to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

EXAMPLES

The following examples are given to enable those skilled in the art to more clearly understand and to practice the present invention. They should not be considered as limiting the scope of the invention, but merely as being illustrative and representative thereof.

Example 1

[1R-(1α,3aβ,7aα)]-Octahydro-7a-methyl-1-[1-[4-methyl-4-[trimethylsilyloxy]-2-pentynyl]cycloprop]-4H-indene-4-one

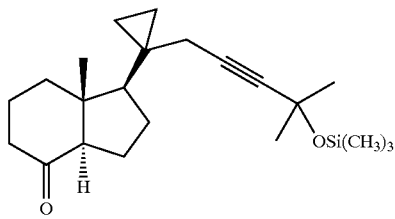

Step 1

Cold dimethylaluminum chloride (34.5 ml, 34.5 mmol, 1M solution in hexanes) was added dropwise to a suspension of [1R-(1α,3aβ,4α,7aα)](1,1-dimethylethyl)dimethyl[[(octahydro-7a-methyl-1-(1-methylethenyl)-1H-inden-4-yl]oxy]silane(9.25 g, 30 mmol) and paraformaldehyde (1.03 g, 34.5 mmol) in dichloromethane (90 ml) at −20° C. The reaction mixture was stirred at 10° C. for 1 h and then poured on ice and acidified with 0.1N hydrochloric acid (100 ml). After 15 min., the reaction mixture was extracted into hexanes and the extracts were washed with brine, dried over magnesium sulfate and concentrated in vacuo to give 9.67 g of a colorless gum. Flash chromatography on silica gel with 25% ethyl acetate/hexanes as the eluant gave 8.93 g of a colorless gum. 1.0 g of this material was purified by HPLC to give [1R-(1α, 3aβ,4α,7aα)]-4-[[(1,1-dimethylethyl)dimethylsilyl]oxy]octahydro-7a-methyl-γ-methylene-1H-indene-1-propanol(0.93 g):mp 38–40° C.; $[α]^{25}D=+26.7°$; IR (CHCl$_3$) 3630 and 1635 cm$^{-1}$; $^1$H NMR (CDCl$_3$) δ 0.01 (3 H, s), 0.011 (3 H, s), 0.80 (3 H, s), 0.88 (9 H, s), 1.15 (1 H, m), 1.3–1.63 (5 H, m), 1.65–1.76 (6 H, m), 2.0 (1 H, m), 2.27 (2 H, m), 3.68 (2 H, t, J=6.0 Hz), 4.01 (1 H, s), 4.91 (1 H, s), 4.95 (1 H, s); MS m/z 339 (M$^+$+H, 40). Anal. Calcd. for C$_{20}$H$_{38}$O$_2$Si: C, 70.94; H, 11.31; Si, 8.29. Found: C, 70.95; H, 11.62; Si, 8.30.

Step 2

To a mixture of [1R-(1α, 3aβ,4α,7aα)]-4-[[(1,1-dimethylethyl)dimethylsilyl]oxy]-octahydro-7a-methyl-γ-methylene-1H-indene-1-propanol (5.07 g, 15 mmol), [prepared as described in Step 1 above] and diiodomethane (13.39 g, 50 mmol) in dichloromethane (45 ml) at −10° C. was added a cold (−1° C.) solution of diethylzinc (45 ml, 45 mmol, 1 M solution in toluene). The reaction mixture was stirred at 5–7° C. for 4.25 h and then poured into a mixture of hexanes (25 ml) and 0.1 N sulfuric acid (150 ml). The product was extracted into hexanes and the extracts were washed with brine, dried over magnesium sulfate and evaporated in vacuo to give 5.34 g of a pale yellow gum. Flash chromatography on silica gel with 30% ethyl acetate/hexanes as the eluant gave 4.91 g of crude product which was further purified by HPLC (15–30 μm mesh silica, 50×50 mm column, 70 ml/min, flow rate) with 20% ethyl acetate in hexanes as eluant to give pure [1R-(1α,3aβ,4α,7aα)]-1-[4-[[1,1-dimethylethyl)dimethysilyl]oxy]octahydro-7a-methyl-1H-inden-1-yl]cyclopropaneethanol (4.13 g): mp 65–66° C.; $[α]^{25}D=+69.17°$ (CHCl$_3$, c=1.33); IR (CHCl$_3$) 3620 cm$^{-1}$; $^1$H NMR (CDCl$_3$) δ 0.04 (3 H, s), 0.06 (3 H, s), 0.80 (1 H, m), 0.22 (2 H, m), 0.69 (1 H, m), 0.88 (9 H, s), 0.92 (2 H, m), 0.94 (3 H, s). 1.20–1.55 (8 H, m), 1.64 (1 H, br d), 1.78–1.92 (2 H, m), 2.02 (1 H, d, J=12 Hz), 2.30 (1 H, m), 3.76 (2 H, br, t of t), 3.97 (1 H, s); MS m/z 353 (M$^+$+H, 70). Anal. Calcd. for C$_{21}$H$_{40}$O$_2$Si: C, 71.53; H, 11.43; Si, 7.96. Found: C, 71.48; H, 11.67, Si, 7.93.

Step 3

[1R-(1α,3aβ,4α,7aα)]-1-[4-[[1,1-dimethylethyl)dimethylsilyl]oxy]octahydro-7a-methyl-1H-inden-1-yl] cyclopropaneethanol (1.056 g, 3.0 mmol,), [prepared as described in Step 2 above] was added to a suspension of pyridinium chlorochromate (1.132 g, 5.246 mmol) and anhydrous sodium acetate (0.430 g, 5.244 mmol) in dichloromethane (15 ml) and the reaction mixture was stirred at room temperature. After 2 h, the reaction mixture was diluted with ether (35 ml), stirred for an additional 15 min., and then filtered through a pad of Florisil. The Florisil pad was washed with ether and the combined filtrate was concentrated in vacuo to give 0.93 g of a solid. Flash chromatography of the solid on a silica gel column with 10% ethyl acetate in hexanes as the eluant gave [1R-(1α,3aβ,4α,7aα)]-1-[4-[[1,1-dimethylethyl)dimethylsily]oxy]octahydro-7a-methyl-1H-inden-1-yl]cyclopropaneacetaldehyde (0.86 g): mp 74–75° C.; $[α]^{25}D=93.73°$ (CHCl$_3$, c=1.18); IR (CHCl$_3$) 1720 cm$^{-1}$; $^1$H NMR (CDCl$_3$) δ 0.00 (3H, s), 0.01 (3H, s), 0.27 (1H, m), 0.32 (1H, m), 0.50 (1 H, m), 0.80 (1 H, m), 0.88 (9 H, s), 0.97 (3H, s), 1.03 (1H, m), 1.15 (1H, m), 1.20–1.55 (6H, m), 1.60–1.75 (2 H, m), 1.80 (1H, d, J=16 Hz), 1.95 (1 H, d, J=12 Hz), 2.89 (1 H, d, J=16 Hz), 3.97 (1 H, s), 9.81 (1 H, d, J=3 Hz); MS m/z 351 (M$^+$+H, 20). Anal. Calcd. for C$_{21}$H$_{38}$O$_2$Si: C, 71.94; H, 10.92; Si, 8.01. Found: C, 71.71; H, 11.15, Si, 8.23.

Step 4

A solution of diethyldiazomethyl phosphonate (1.78 g, 10 mmol) in anhydrous tetrahydrofuran (6 ml) was added to a solution of potassium t-butoxide (1.234 g, 10.9 mmol) in anhydrous tetrahydrofuran (20 ml) at −70° C. After 25 min., a solution of [1R-(1α,3aβ,4α,7aα)]-1-[4-[[1,1-dimethylethyl)dimethylsilyl]oxy]octahydro-7a-methyl-1H-inden-1-yl]cyclopropaneacetaldehyde (2.103 g, 6.0 mmol), [prepared as described in Step 3 above] in tetrahydrofuran (6.0 ml) was added. After 1 h, the cooling bath was removed and the stirring was continued for an additional 1.5 h. A solution of saturated ammonium chloride (10 ml) was added. After 15 min., the reaction mixture was poured into a mixture of ether (100 ml) and saturated ammonium chloride (60 ml). The organic phase was separated and washed with brine, dried over magnesium sulfate and evaporated in vacuo to give 2.18 g of a gum. Purification by flash chromatography on silica gel column with 2.5% ethyl acetate in hexanes as the eluant gave as a crystalline solid which was slurried with methanol and filtered to give [1R-(1α,3aβ,4α,7aα)][(1,1-dimethylethyl)dimethyl[[octahydro-7a-methyl-1-[1-(2-propynyl)cyclopropyl]-1H-inden-4-yl]oxy]silane (1.77 g): mp 49–50° C.; $[α]^{25}D=58.64°$ (CHCl$_3$, c=1.03); IR (CHCl$_3$) 3307 cm$^{-1}$; $^1$H NMR (CDCl$_3$) δ −0.01 (3 H, s), 0.00 (3 H, s), 0.22 (2 H, m), 0.38 (1 H, m), 0.69 (1 H, m), 0.87 (9 H, s), 0.94 (3 H, s), 0.96 (1 H, m), 1.25–1.55 (7 H, m), 1.64 (1 H, br d, J=12 Hz), 1.75–1.90 (3 H, m), 1.95 (1 H, d, J=16 Hz), 1.96 (1H, s), 2.69 (1 H, d, J=16 Hz), 3.98 (1 H, s); MS m/z 346 (M$^+$, 20). Anal. Calcd. for C$_{21}$H$_{38}$OSi: C, 76.23; H, 11.05; Si, 8.10. Found: C, 76.03; H, 10.84; Si, 8.12.

Step 5 n-Butyllithium (5.5 ml, 8.8 mmol, 1.6 M solution in hexanes) was added to a solution of [1R-(1α,3aβ,4α,7aα)][(1,1-dimethylethyl)dimethyl[[octahydro-7a-methyl-1-[1-

(2-propynyl)cyclopropyl]-1H-inden-4-yl]oxysilane (1.73 g, 5.0 mmol), [prepared as described in Step 4 above] in anhydrous tetrahydrofuran (18 ml) at −78° C. After 30 min., acetone (5.8 g, 100 mmol) was added and the stirring was continued for an additional 30 min. The cooling bath was removed and after 3 h additional amounts of acetone (2.9 g, 50 mmol) was added. After 1.5 h, the reaction mixture was quenched with saturated ammonium chloride (15 ml) and then poured into a mixture of ether (100 ml) and saturated ammonium chloride (60 ml). The organic layer was separated and washed with brine, dried over sodium sulfate and evaporated in vacuo to give 2.12 g of a colorless gum. Purification by flash chromatography on a silica gel column using 15% ethyl acetate in hexanes as eluant gave [1R-(1α,3aβ,4α,7aα)]-5-[1-[4-[[1,1-dimethylethyl)dimethylsilyl]oxy]octahydro-7a-methyl-1H-inden-1-yl]cyclopropyl]-2-methyl-3-pentyn-2-ol as a colorless gum (1.67 g); $[\alpha]^{25}D=+39.09°$ (EtOH, c=1.036); IR (CHCl$_3$) 3602 cm$^{-1}$; $^1$H NMR (CDCl$_3$) δ −0.01 (3 H, s), 0.00 (3 H, s), 0.20 (2 H, m), 0.40 (1 H, m), 0.62 (1 H, m), 0.87 (9 H, s), 0.93 (3 H, s), 1.00 (1 H, m), 1.2–1.4 (13 H, m), 1.49 (6 H, s), 1.62–1.95 (5 H, m), 2.03 (1 H, d, J=17 Hz), 2.62 (1 h, d, J=17 Hz), 3.97 (1 H, s); MS m/z 404 (M$^+$, 18). Anal. Calcd. for C$_{25}$H$_{44}$O$_2$Si: C, 74.28; H, 10.96; Si, 6.94. Found: C, 73.92; H, 11.22; Si, 6.87.

Step 6

Fluorosilicic acid (3.75 ml, 30% aqueous solution prepared as described in Pilcher, A. S. and DeShong, P. J. Org. Chem., 58, 5130 (1993)) was added to a solution of [1R-(1α,3aβ,4α,7aα)]-5-[1-[4-[[1,1-dimethylethyl)dimethylsilyl]oxy]octahydro-7a-methyl-1H-inden-1-yl]cyclopropyl]-2-methyl-3-pentyn-2-ol (0.8 g, 2.0 mmol), [prepared as described in Step 5 above] in acetonitrile (12 ml) at 0° C. and the reaction mixture was allowed to warm to 15° C. After 3.5 h, the reaction mixture was diluted with water (10 ml) and ethyl acetate (10 ml) and then poured into a mixture of ethyl acetate (100 ml) and water (50 ml). The organic layer was separated and washed with brine, saturated sodium bicarbonate, dried over sodium sulfate and evaporated in vacuo to give a gum. Purification by flash chromatography on a silica gel column using 25% ethyl acetate in hexanes as eluant gave [1R-(1α,3aβ,4α,7aα:)] octahydro-1-[1-(4-hydroxy-4-methyl-2-pentyl)cyclopropyl]-7a-methyl-4H-inden-4-ol as a crystalline solid (0.5 g): mp 97–98° C.; $[\alpha]^{25}D=36°$ (MeOH, c=1.03); IR (CHCl$_3$) 3604, 2230 cm$^{-1}$; $^1$H NMR (CDCl$_3$) δ 0.22 (2 H, m), 0.39 (1 H, m), 0.63 (1 H, m), 0.97 (3 H, s), 1.07 (1 H, m), 1.2–1.45 (8 H, m), 1.50 (6 H, s), 1.79–1.90 (3 H, m), 2.01 (1 H, m), 2.03 (1 H, m), 2.01 (1 H, m), 2.03 (1 H, d, J=17 Hz), 2.62 (1 H, d, J=17 Hz), 4.06 (1 H, s); MS m/z 581 (2×M$^+$+H). Anal. Calcd. for C$_{19}$H$_{30}$O$_2$: C, 78.57; H, 10.41. Found: C, 78.54; H, 10.54.

Step 7

Pyridinium dichromate (3.30 g, 8.77 mmol) was added to a solution of [1R-(1α,3aβ,4α,7aα)]octahydro-1-[1-(4-hydroxy-4-methyl-2-pentynyl)cyclopropyl]-7a-methyl-4H-inden-ol (0.8 g, 2.75 mmol), ), [prepared as described in Step 6 above] in dichloromethane (16 ml) and the reaction mixture was stirred at room temperature. After 3.5 h, additional amounts of dichloromethane (2.5 ml) and pyridinium dichromate (2.0 g, 5.3 mmol) were added and the stirring was continued for an additional 2.5 h. The reaction mixture was diluted with ether (25 ml), stirred for 30 min., and then filtered through a pad of Celite. The Celite pad was washed with ether and the filtrate was concentrated in vacuo to give 0.75 g of a pale yellow gum. Purification by flash chromatography on a silica gel column using 50% ethyl acetate in hexanes as eluant gave [1R-(1α,3aβ,7aα)]octahydro-1-[1-[4-hydroxy-4-methyl-2-pentynyl)cyclopropyl]-7a-methyl-4H-inden-4-one (0.70 g) as a colorless gum: $[\alpha]^{25}D=−5.5°$ (MeOH, c=1.2); IR (CHCl$_3$) 3602, 2232, 1706 cm$^{-1}$; $^1$H NMR (CDCl$_3$) δ 0.31 (2 H, m), 0.44 (1 H, m), 0.62 (1 H, m), 0.68 (3 H, s), 1.14 (1 H, m), 1.53 (6 H, s), 1.73 (2 H, m), 1.83 (1 H, s, OH), 1.96 (1 H, m), 2.04 (1 H, m), 2.05 (1 H, d, J=17 Hz), 2.16–2.29 (4 H, m), 2.50 (1 H, dd, J=7.6 Hz), 2.62 (1 H, d, J=17 Hz); MS (E/I) m/z 288.2092. Anal. Calcd. for C$_{19}$H$_{28}$O$_2$: C, 79.12; H, 9.78. Found: C, 78.93; H, 9.80.

Step 8

A solution of [1R-(1α,3aβ,7aα)]octahydro-1-[1-[4-hydroxy-4-methyl-2-pentynyl) cyclopropyl]-7a-methyl-4H-inden-4-one (0.7 g, 2.426 mmol), [prepared as described in Step 7 above] and 1-(trimethylsilyl)imidazole (2.6 ml, 17.7 mmol) in methylene chloride (15 ml) was stirred under an argon atmosphere at room temperature for 18 h and then quenched with water (10 ml). After 25 min., the reaction mixture was poured into a mixture of ether (100 ml) and water (50 ml). The organic phase was collected and the aqueous phase was re-extracted with ether. The combined organic extracts were washed with brine, dried over sodium sulfate and evaporated to give 0.82 g of a colorless oil. Purification by flash chromatography on silica gel with 20% ethyl acetate in hexane as eluant gave [1R-(1α,3aβ,7aα)] octahydro-7a-methyl-1-[1-4-methyl-4-[trimethylsilyloxy]-2-pentynyl]cyclopropyl]-4H-inden-4-one(0.79 g, 90%) as an oil: $[\alpha]^{25}D=−10.69°$ (EtOH, c=0.8151); IR (CHCl$_3$) 2250 and 1706 cm$^{-1}$; $^1$H NMR CDCl$_3$) δ 0.18 (9 H, s), 0.28 (2 H, m), 0.32 (1 H, m), 0.62 (1 H, m), 0.69 (3 H, s), 1.13 (1 H, m), 1.47 (3 H, s), 1.48 (3 H, s) 1.50–1.58 (2 H, m), 1.70–1.76 (2 H, m), 1.92–1.99 (1 H, m), 2.00 (1 H, d, J=17 Hz), 2.05 (1 H, m), 2.51 (1 H, m), 2.64 (1 H, d, J=17 Hz); MS m/z 361 (11). Anal. Calcd. for C$_{22}$H$_{36}$O$_2$Si: C, 73.28; H, 10.06; Si, 7.79. Found: C, 73.28; H, 10.10; Si, 7.79.

Example 2

1,25-Dihydroxy-23-yne-20,21,28-cyclopropyl-cholecalciferol

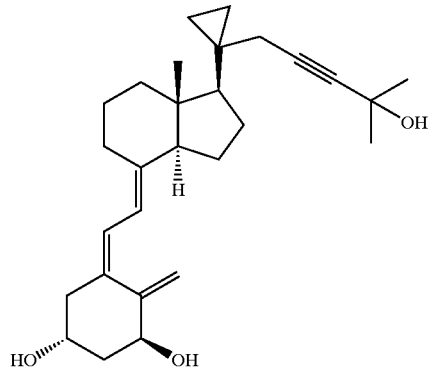

Step 1 n-Butyllithium (0.5 ml, 0.8 mmol, 1.6 M solution in hexane) was added to a solution of [3S-(1Z,3α,5β)]-[2-[3,5-bis[[1,1-dimethylethyl)dimethylsilyl]oxy]-2-methylene-cyclohexylidene]ethyl]diphenylphosphine oxide (0.465 g, 0.79 mmol) (see Kigel, J. et al. Tetr. Lett., 32:6057–6060 (1991)), in anhydrous tetrahydrofuran (5.0 ml) at −78° C. The resultant deep red solution was stiffed at −72° C. for 7 min., and then treated with a solution of [1R-(1α,3aβ,7aβ)] octahydro-7a-methyl-1-[1-[4-methyl-4-[(trimethylsilyl)oxy]-2-pentynyl]-cyclopropyl]-4H-inden-4-one (0.18 g, 0.5 mmol) [prepared as described in Example 1] in anhydrous tetrahydrofuran (4.0 ml). After 3 h, the reaction mixture was quenched with a 1:1 mixture of 2 N Rochelle salt solution and 2 N potassium bicarbonate solution (10 ml). The reaction mixture was allowed to warm to room temperature and then poured into ethyl acetate (100 ml) and a 1:1 mixture of Rochelle salt solution and 2 N potassium bicarbonate solution (50 ml). The organic phase was separated and the aqueous phase was extracted with ethyl acetate. The combined organic extracts were washed with brine, dried over sodium sulfate and evaporated to give 0.89 g of residue. Purification by flash chromatography on silica gel with 5% ethyl acetate-hexanes as eluant gave a trisilyl intermediate (0.34 g), which was used directly in the next step.

Step 2

A solution of the trisilyl intermediate (0.33 g, 0.455 mmol), [prepared as described in Step 1 above] and tetrabutylammonium fluoride (3.3 ml, 3.3 mmole, 1.0 M solution in tetrahydrofuran) in anhydrous tetrahydrofuran (3.3 ml) was stirred at room temperature under argon atmosphere. After 17 h, the reaction mixture was diluted with water (10 ml). After 10 min., the reaction mixture was poured into a 1:1 mixture of brine and water and the organic phase was collected. The aqueous phase was re-extracted with ethyl acetate and the combined organic extracts were washed with brine, dried over sodium sulfate, and evaporated to give 0.19 g of a gum. Purification by flash chromatography on silica gel column with ethyl acetate as eluant gave 0.144 g of a colorless residue which was dissolved in anhydrous methyl formate (5 ml) and filtered through a 0.45 μm filter. The filtrate was evaporated at 40° C. and the residue was kept under high vacuum (0.2 mm of Hg) for 4 h to give 1,25-dihydroxy-23-yne-20,21,28-cyclopropyl-cholecalciferol (0.13 g) as a colorless foam: $[\alpha]_D^{23}$=−10.23° (EtOH, c=0.38); $\lambda_{max}$ (MeOH) 264 (ε=16859), 248 (sh, 15198), 212 (ε=15127); $^1$H NMR (CDCl$_3$) δ 0.26 (2 H, m), 0.41 (1 H, m), 0.56 (1 H, m), 0.59 (3 H, s), 1.1 (1 H, m), 1.40–1.49 (8 H, m), 1.50 (6 H, s), 1.70 (2 H, m), 1.84 (1 H, s, OH), 1.96 (1 H, m), 2.0 (4 H, m), 2.05 (1 H, d, J=17 Hz), 2.31 (1 H, m), 2.60 (1 H, d, J=17 Hz), 2.61 (1 H, m), 2.80 (1 H, m), 4.23 (1 H, br s), 4.42 (1 H, br s), 4.99 (1 H, s), 5.33 (1 H, s), 5.98 (1 H,d, J=11 Hz), 6.37 (1 H, d, J=11 Hz); MS (FAB) m/z 424 (M$^+$ 52).

Example 3

1,25-Dihydroxy-23-yne-20,21,28-cyclopropyl-19-nor-cholecalciferol

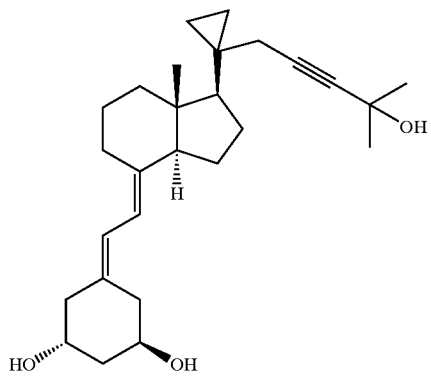

Step 1 n-Butyllithium (0.55 ml, 0.81 mmol, 1.6 M solution in hexanes) was added to a solution of [3 R-(3α,5β, Z)-3,5-bis[[1,1-dimethylethyl)dimethylsilyl]oxy]cyclohexylidene]-ethyl]diphenylphosphine oxide (0.51 g, 0.79 mmol) (see Perlman, K. L., et al., Tetr. Lett., 32:7663–7666 (1991)), in anhydrous tetrahydrofuran (5 ml) at −78° C. under an argon atmosphere. The resultant deep red solution was stirred at −68° C. for 10 min., and then treated with a solution of [1R-(1α,3aβ,7aα)octahydro-7a-methyl-1-[1-[4-methyl-4-[trimethylsilyl-oxy]-2-pentynyl]cyclopropyl]-4H-inden-4-one (0.18 g, 0.5 mmol), [prepared as described in Example 1] in anhydrous tetrahydrofuran (4.0 ml). The reaction mixture was stirred at −78° C. for 4 h, then allowed to warm to 20° C. and quenched with a 1:1 mixture of 1 N Rochelle salt solution and 1 N potassium bicarbonate solution (10 ml). After 10 min., the reaction mixture was poured into ethyl acetate (100 ml) and 1:1 mixture of IN Rochelle salt solution and 1 N potassium bicarbonate solution (50 ml). The organic phase was collected and the aqueous phase was re-extracted with ethyl acetate. The combined organic extracts were dried over sodium sulfate and evaporated to give 0.59 g of a gum. Purification by flash chromatography on silica gel column with 5% ethyl acetate in hexane as eluant gave the trisilyl intermediate (0.31 g) which was used in the next step without further purification.

Step 2

The trisilyl intermediate (0.30 g, 0.42 mmol), [prepared as described in Step 1 above] was dissolved in anhydrous tetrahydrofuran (3.0 ml) and treated with tetrabutylammonium fluoride (3.5 ml, 3.5 mmol, 1M solution in tetrahydrofuran). The reaction mixture was stirred at room temperature under an argon atmosphere for 48 h, then diluted with water (10 ml) and stirred for an additional 10 min. The reaction mixture was then poured into ethyl acetate (75 ml) and a 1:1 mixture of brine/water (50 ml). The organic phase was collected and the aqueous phase was re-extracted with ethyl acetate. The combined organic extracts were dried over sodium sulfate and evaporated to give 0.24 g of a residue. Purification of the residue by flash chromatography on a silica gel column using ethyl acetate as eluant gave crude product which was dissolved in methyl formate (5.0 ml) and filtered through a 0.45 μm filter. The organics were evaporated and the residue was dried under high vacuum (0.2 Torr) at room temperature for 5 h to give 1,25-dihydroxy-23-yne-20,21,28-cyclopropyl-19-nor-cholecalciferol (0.15 g) as a colorless foam: $[\alpha]_D^{23}$=+52.3° (EtOH, c=0.45); $\lambda_{max}$ (MeOH) 261 (ε=25929), 251 (ε=38263), 243 (ε=22011), 227 (sh, ε=13396); $^1$NMR (CDCl$_3$) δ 0.28 (2 H, m), 0.40 (1 H, m), 0.55 (1 H, m), 0.58 (3 H, s), 1.11 (1 H, m), 1.40–1.48 (2 H, m), 1.50 (6 H, s), 1.55–1.60 (5 H, m), 1.68 (2 H, m), 1.80 (2 H, m), 1.90–2.05 (4 H, m), 2.10 (1 H, d,J=17 Hz), 2.20 (2 H, m), 2.50 (1 H,d, J=16 Hz), 2.60 (1 H,d, J=17 Hz), 4.06 (1 H, br s), 4.11 ( H, br s), 5.82(1 H,d, J=11 Hz), 6.30(1 H,d, J=11 Hz); MS (FAB)m/z 412 (M$^+$).

Example 4

[(1R-(1α,3aβ,7aα)]Octahydro-7a-methyl-1-[1-[5,5,5-trifluoro-4-hydroxy-4-((trifluoromethyl)-2-pentynyl]cyclopropyl]-4H-inden-4-one

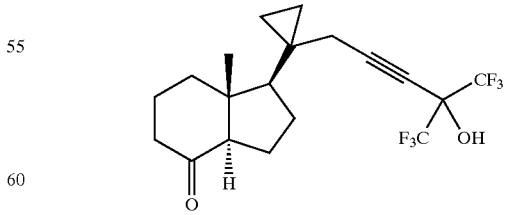

Step 1 n-Butyllithium (7.5 ml, 12 mmol, 1.6 M solution in hexanes) was added to a solution of [1R-(1α, 3aβ,4α, 7aα)] [(1,1-dimethylethyl)dimethyl[[octahydro-7a-methyl-1-[1-

(2-propynyl)cyclopropyl)]-1H-inden-4-yl]oxy]silane (2.36 g, 6.25 mmol), [prepared as described in Example 1, Step 4] in anhydrous tetrahydrofuran (25 ml) at −70° C. After 45 min., hexafluoroacetone (5.8 ml, 100 mmol) that had been condensed into an addition funnel capped with a dry-ice condenser was added and stirring was continued. After 1.5 h, the reaction mixture was quenched with 2 N Rochelle salt solution (20 ml), the reaction mixture was allowed to warm to room temperature and then poured into a mixture of ethyl acetate (125 ml) and 50% brine (75 ml). The organic layer was separated and washed with brine, dried over sodium sulfate and evaporated in vacuo to give 5.8 g of a colorless gum. Purification by flash chromatography on a silica gel column using 15% ethyl acetate in hexanes as eluant gave [1R-(1α,3aβ,4α,7aα)]-5-[1-[4-[[1,1-dimethylethyl) dimethylsily]-oxy]octahydro-7a-methyl-1H-inden-1-yl] cyclopropyl]-1,1,1-trifluoro-2-(trifluoromethyl)-3-pentyn-2-ol (3.6 g) as a colorless oil: $[\alpha]^{25}D=+7.69°$ (EtOH, c=4.0); IR (CHCl$_3$) 3588, 2241 cm$^{-1}$; $^1$H NMR (CDCl$_3$) δ 0.04 (6 H, s), 0.19 (1 H, m), 0.28 (1 H, m), 0.36 (1 H, m), 0.70(1 H, m), 0.86 (9 H, s), 0.93 (3 H, s), 1.00 (1 H, q, J=11 Hz), 1.2–1.59 (7 H, m), 1.64–1.92 (4 H, m), 2.06 (1 H, d, J=17 Hz), 2.75 (1 H, d, J=17 Hz), 3.13 (1 H, s, OH), 3.96 (1 H, s); MS m/z 512 (M$^+$, 18). Anal. Calcd. for C$_{25}$H$_{38}$F$_6$O$_2$Si: C, 58.57; H, 7.47; F, 22.24, Si, 5.48. Found: C, 58.39; H, 7.57, F, 22.34, Si, 5.41.

Step 2

Fluorosilicic acid (6.0 ml, 30% aqueous solution prepared as described in Pilcher, A. S. and DeShong, P. J. Org. Chem., 58, 5130 (1993)) was added to a solution of [1R-(1α,3aβ, 4α,7aα)]-5-[1-[4-[[1,1-dimethylethyl)dimethylsilyl]oxy] octahydro-7a-methyl-1H-inden-1-yl]cyclopropyl]-1,1,1-trifluoro-2-(trifluoromethyl)-3-pentyn-2-ol (1.24 g, 2.40 mmol), [prepared as described in Step 1 above] in acetonitrile (18 ml) and the reaction mixture was stirred at room temperature under an argon atmosphere. After 2.5 h, the reaction mixture was poured into a mixture of ethyl acetate (100 ml) and saturated sodium bicarbonate (50 ml). The organic layer was separated and washed with brine, dried over sodium sulfate and evaporated in vacuo to give 0.9 g of a partially crystalline solid. Purification by flash chromatography on a silica gel column using 25% ethyl acetate in hexanes as eluant gave [1R-(1α,3aβ,4α,7aα)]-octahydro-7a-methyl-1-[1-[5,5,5-trifluoro-4-hydroxy-4-(trifluoromethyl)-2-pentynyl]-cyclopropyl]-4H-inden-4-ol as crystalline solid (0.65 g): mp 96–97° C.; $[\alpha]^{25}D=25.39°$ (EtOH, c=0.957); IR (CHCl$_3$) 3590, 2266, 2241 cm$^{-1}$; $^1$H NMR (CDCl$_3$) δ 0.22 (1 H, m), 0.32 (1 H, m), 0.42 (1 H, m), 0.71 (1 H, m), 0.98 (3 H, s), 1.04 (1 H, m), 1.26–1.33 (2 H, m), 1.40–1.60 (6 H, m), 1.84–1.98 (4 H, m), 2.01 (1 H, d, J=17 Hz), 2.76 (1 H, d, J=17 Hz), 3.86 (1 H, s, OH), 4.08 (1 H, s); MS m/z 397 (M$^+$-H). Anal. Calcd. for C$_{19}$H$_{24}$F$_6$O$_2$: C, 57.28; H, 6.07; F, 28.61. Found: C, 57.34; H, 5.97; F, 28.66.

Step 3

To a stirred solution of [1R-(1α,3aβ,4α,7aα)]octahydro-7a-methyl-1-[5,5,5-trifluoro-4-hydroxy-4-(trifluoromethyl)-2-pentynyl]cyclopropyl]-4H-inden-4-ol (0.66 g, 1.65 mmol), [prepared as described in Step 2 above] in methylene chloride (14 ml) was added pyridinium dichromate (4.0 g, 10.63 mmol) and the reaction mixture was stirred at room temperature for 4 h. Additional amounts of pyridinium dichromate (0.5 g, 1.32 mmol) was added and the stirring was continued for 30 min. Diethyl ether (25 ml) was added and the reaction mixture was filtered over Celite pad, and the Celite pad was then washed with diethyl ether. The combined filtrate and washings were washed with 1N potassium bicarbonate (100 ml), followed by a 1:1 mixture of brine/water. The aqueous washings were back-extracted with ethyl acetate and the combined organic extracts were dried over sodium sulfate and evaporated to give 0.64 g of partially crystalline material. Flash chromatography on silica gel column with 25% ethyl acetate in hexanes as the eluant gave [(1R-(1α,3aβ,7aα)]octahydro-7a-methyl-1-[1-[5,5,5-trifluoro-4-hydroxy-4-(trifluoromethyl)-2-pentynyl] cyclopropyl]-4H-inden-4-one (0.56 g, 86%) as colorless crystals. Crystallization of 65 mgs of the product from 50% ether in hexane gave [(1R-(1α, 3aβ,7aα)]octahydro-7a-methyl-1-[1-[5,5,5-trifluoro-4-hydroxy-4-(trifluoromethyl)-2-pentynyl]cyclopropyl]-4H-inden-4one (51 mg) as colorless needles: mp 145–146° C.; $[\alpha]^{26}D=-8.52°$ (EtOH, c=0.704); IR (CHCl$_3$) 3588, 2268, 2242, and 1707 cm$^{-1}$; $^1$H NMR(CDCl$_3$) δ 0.30 (1 H, m), 0.38 (1 H, m), 0.45 (1 H, m), 0.68 (3 H, s), 1.13 (1 H, q, J=14 Hz), 1.55 (2 H, m), 1.73 (2 H, m), 1.95 (1 H, m), 2.11–2.31 (4 H, m), 2.13 (1 H, d, J=17 Hz), 2.50 (1 H, m), 2.75 (1 H, d, J=17 Hz), 3.88 (1 H, s, OH); MS m/z 396. Anal. Calcd for C$_{19}$H$_{22}$F$_6$O$_2$: C, 57.47; H, 5.59; F, 28.76. Found: C, 57.60, H, 5.65; F, 28.66.

Example 5

1,25-Dihydroxy-23-yne-26,27-hexafluoro-20,21,28-cyclopropyl-cholecalciferol

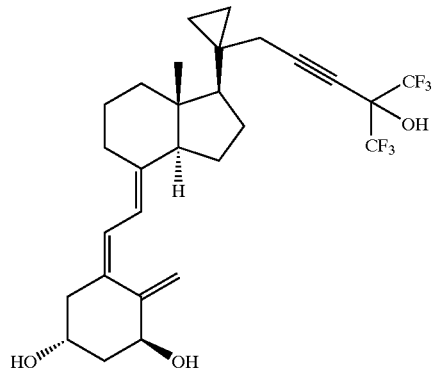

Step 1 n-Butyllithium (0.52 ml, 0.81 mmol, 1.6 M solution in hexane) was added to a stirred solution of [3S-(1Z,3α,5β)]-[2-[3,5-bis[[1,1-dimethylethyl)dimethylsilyl]oxy]-2-methylenecyclohexylidene]ethyl]diphenylphosphine oxide (0.475 g, 0.81 mmol) in anhydrous tetrahydrofuran (5.0 ml) at −78° C. The resultant deep red solution was stirred at −78° C. under argon for 8 min and then treated with a solution of [1R-(1α,3aβ,7aα)]octahydro-7a-methyl-1-[1-[5,5,5-trifluoro-4-hydroxy-4-(trifluoromethyl)-2-pentynyl] cyclopropyl]-4H-inden-4-one (0.16 g, 0.4 mmol), [prepared as described in Example 4] in anhydrous tetrahydrofuran (2.0 ml). After 3 h, the reaction mixture was allowed to warm to 10° C. and then quenched with a 1:1 mixture of 1 N Rochelle salt solution and 1 N potassium bicarbonate solution (10 ml). After 10 min., the reaction mixture was poured into ethyl acetate (100 ml) and a 1:1 mixture of 1 N Rochelle salt solution and 1 N potassium bicarbonate solution (50 ml). The organic phase was collected and the aqueous phase was re-extracted with ethyl acetate. The combined organic extracts were dried over sodium sulfate and evaporated to give 0.55 g of a gum. Purification by flash chromatography on silica gel column with 20% ethyl acetate in hexane as eluant gave 0.15 g of the trisilyl intermediate as colorless gum, which was used without purification in the next step.

Step 2

Tetrabutylammonium fluoride (2.5 ml, 2.5 mmol, 1M solution in tetrahydrofuran) was added to a solution of the trisilyl intermediate (0.145 g, 0.19 mmol) in anhydrous tetrahydrofuran (3.0 ml) and the reaction mixture was stirred at room temperature under an argon atmosphere. After 19 h, the reaction mixture was diluted with water (10 ml), stirred for an additional 10 min. and then poured into a mixture of ethyl acetate (75 ml) and a 1:1 mixture of brine/water (50 ml). The organic phase was collected and the aqueous phase was re-extracted with ethyl acetate. The combined organic extracts were dried over sodium sulfate and evaporated to give 0.16 g of residue. Purification by flash chromatography on silica gel column with ethyl acetate as eluant gave a solid which was dissolved in methyl formate (2.0 ml) and filtered through a 0.45 μm filter. The filtrate was evaporated at 40° C. and kept under high vacuum at room temperature for 6 h to give 1,25-dihydroxy-23-yne-26,27-hexafluoro-20,21,28-cyclopropyl-cholecalciferol (93 mgs) as a colorless foam: $[\alpha]D^{25}=-1.12$ (EtOH, c=0.50); $\lambda_{max}$ (MeOH) 264 ($\epsilon$=16762), 247 (sh, $\epsilon$=14746), 213 ($\epsilon$=13727); $^1$H NMR (CDCl$_3$) δ 0.28 (1 H, m), 0.35 (1 H, m), 0.41 (1 H, m), 0.59 (3 H, s), 0.64 (1 H, m), 1.09 (1 H, m), 1.40–1.60 (7 H, m), 1.65–1.78 (2 H, m), 1.90–2.05 (5 H, m), 2.18 (2 H, d, J=17 Hz), 2.31 (1 H, dd, J=14, 7 Hz), 2.63 (1 H, d, J=14 Hz), 2.73 (1 H, d, J=17 Hz), 2.85 (1 H, m), 3.45 (1 H, s, OH), 4.23 (1 H, br s), 4.43 (1 H, br s), 5.00 (1 H, s), 5.32 (1 H, s), 6.00 (1 H, d, J=11 Hz), 6.37 (1 H, d, J=11 Hz); MS (FAB) m/z 532 (M$^+$50).

Example 6

1,25-Dihydroxy-23-yne-26,27-hexafluoro-20,21,28-cyclopropyl-19-nor-cholecalciferol

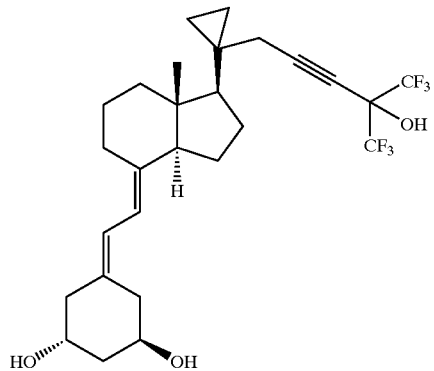

Step 1 n-Butyllithium (0.5 ml, 0.80 mmol, 1.6 M solution in hexane) was added to a stirred solution of [3R-(3α,5β,Z)-3,5-bis[[1,1-(dimethylethyl)dimethylsilyl]oxy]cyclohexylidene]-ethyl]diphenylphosphine oxide (0.45 g, 0.79 mmol) in anhydrous tetrahydrofuran (5.0 ml) at −78° C. The resultant deep red solution was stirred at −78° C. under argon for 8 min., and then treated with a solution of [1R-(1α,3aβ,7aα)]octahydro-7a-methyl-1-[5,5,5-trifluoro-4-hydroxy-4-(trifluoromethyl)cyclopropyl]-4H-inden-4-one(0.16 g, 0.40 mmol), [prepared as described in Example 4 above] in anhydrous tetrahydrofuran (3.0 ml). The reaction mixture was stirred at −78° C. for 3 h, then allowed to warm to 10° C., and quenched with a 1:1 mixture of 1 N Rochelle salt solution and 1 N potassium bicarbonate solution (10 ml). After 10 min., the reaction mixture was poured into ethyl acetate (100 ml) and a 1:1 mixture of 1 N Rochelle salt solution and 1 N potassium bicarbonate solution (50 ml). The organic phase was collected and the aqueous phase was re-extracted with ethyl acetate. The combined organic extracts were dried over sodium sulfate and evaporated to give 0.54 g of residue. Purification by flash chromatography on a silica gel column with 20% ethyl acetate in hexane as eluant gave 0.15 g of trisilyl intermediate as a colorless gum, which was used without further purification in the next step.

Step 2

Tetrabutylammonium fluoride (2.5 ml, 2.5 mmol, 1M solution in tetrahydrofuran) was added to a solution of above trisilyl intermediate (0.15 g, 0.20 mmol) in anhydrous tetrahydrofuran (3.0 ml). The reaction mixture was stirred under argon at room temperature for 40 h, then diluted with water (10 ml) and poured into ethyl acetate (75 ml) and a 1:1 mixture of brine/water (50 ml). The organic phase was collected and the aqueous phase was re-extracted with ethyl acetate. The combined organic extracts were dried over sodium sulfate and evaporated to give 0.10 g of crude product. Purification by flash chromatography on a silica gel column with ethyl acetate as eluant gave a residue, which was dissolved in methyl formate (5.0 ml), filtered through a 0.45 μm filter. The filtrate was evaporated at 40° C. and dried under high vacuum (0.2 Torr) at room temperature for 6 h to give 1,25-dihydroxy-23-yne-26,27-hexafluoro-20,21,28-cyclopropyl-19-nor-cholecalciferol (95 mg) as a colorless foam: $[\alpha]D^{23}=+36.20°$ (EtOH, c=0.32); $\lambda_{max}$ (MeOH) 243 ($\epsilon$=31322), 251 ($\epsilon$=37316), 260 ($\epsilon$=25430) nm; IR(CHCl$_3$) 3603, 2242 cm$^{-1}$; $^1$H NMR (CDCl$_3$) δ 0.28 (1 H, m), 0.35 (1 H, m), 0.42 (1 H, m), 0.60 (3 H, s), 0.65 (1 H, m), 1.10 (1 H, m), 1.40–1.72 (9 H, m), 1.80 (1 H, m), 1.97 (4 H, m), 2.19 (1 H, d, J=17 Hz), 2.49 (1 H, m), 2.72 (1 H, d, J=17 Hz), 2.75 (2 H, m), 3.40(1 H, br s, OH), 4.05 (1 H, br, s), 4.12 (1 H, br s), 5.82 (1 H, d, J=11 Hz), 6.30 (1 H, d, J=11 Hz); MS (FAB) m/z 520 (M$^+$80).

Example 7

[1R-[1α(Z),3aβ,7aα]]-Octahydro-7a-methyl-1-[1-[5,5,5-trifluoro-4-(trifluormethyl)-4[(trimethylsily)oxy]-2-pentenyl]-cyclopropyl]-4H-inden-4-one

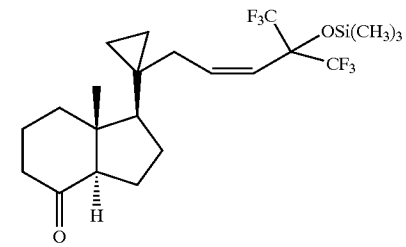

Step 1

A solution of [1R-(1α,3aβ,4α,7aα)]octahydro-7a-methyl-1-[1-[5,5,5-trifluoro-4-hydroxy-4-(trifluormethyl)-2-pentynyl]cyclopropyl]-4H-inden-4-ol(1.195 g) in ethyl acetate (12 ml), hexane (30.0 ml), absolute ethanol (1.2 ml), and quinoline (60 ml) was hydrogenated over Lindlar's catalyst(240 mg) at atmospheric pressure and room temperature. After 2.0 h, the reaction mixture was filtered through a pad of Celite. The Celite pad was washed with ethyl acetate and the combined filtrates were washed with 1.0 N hydrochloric acid (50 ml), brine, dried over magnesium sulfate and evaporated to give 1.16 g of a colorless gummy residue. The residue was purified by flash chromatography on a silica gel column with 40% ethyl acetate in hexanes as eluant to give 1.09 g of a colorless gum which was triturated with hexane to give [1R-[1α(Z),3aβ,4α,7aα]] octahydro-7a-methyl-1-[1-[5,5,5-trifluoro-4-hydroxy-4-(trifluormethyl)-2-pentenyl]cyclopropyl]-4H-inden-4-ol (84 mg): mp 99–100° C.; [α]$D^{25}$+24.49° (MeOH, c=1.03); IR (CHCl$_3$) 3619, 3569, 1659 cm$^{-1}$; $^1$H NMR (CDCl$_3$) δ 0.09 (1 H, m), 0.23 (1 H, m), 0.34(1 H, m), 0.67 (1 H, m), 1.00 (3 H, s), 1.11 (1 H, m), 1.19–130 (2 H, m), 1.37–1.56 (6 H, m), 1.76–1.88 (3 H, m), 2.03 (1 H, d, J=16 Hz), 2.17 (1 H, ddd, J=16,7,6 Hz), 2.95 (1 H, ddd, J=16,7,6), 3.13 (1 H, s, OH), 4.06 (1 H, s), 5.40 (1 H, d, J=12 Hz), 6.10 (1 H, ddd, J=12, 7, 6 Hz); MS m/z 400 (M$^+$, 10). Anal. Calcd for C$_{19}$H$_{26}$F$_6$O$_2$: C, 56.99; H, 6.55; F, 28.47. Found: C, 57.10; H, 6.57; F, 28.31.

Step 2

Pyridinium dichromate (3.3 g, 8.7 mmol) was added to a stirred solution of [1R-[1α(Z),3aβ,4α,7aαa]]octahydro-7a-methyl-1-[1-[5,5,5-trifluoro-4-hydroxy-4-(trifluoromethyl)-2-pentenyl]cyclopropyl]-4H-inden-4-ol (1.00 g, 2.5 mmol) in dichloromethane (25 ml) and the resultant heterogeneous mixture was stirred at room temperature. After 5 h, the reaction mixture was diluted with diisopropyl ether (30 ml), stirred for an additional 15 min., and then filtered through a pad of Celite. The filtrate was evaporated to give 0.984 g of a pale yellow solid. Purification by flash chromatography on a silica gel column with 30% ethyl acetate in hexanes as eluant, gave 0.84 g of a colorless solid. The solid was dissolved in dichloromethane (4 ml) and filtered through a 0.45 mm filter (Millex-HV). The filtrate was diluted with hexane (7.0 ml) and then concentrated to about 6 ml and left at -2° C. overnight. The solid was filtered off to give [1R-[1α(Z),3aβ,7aα]]octahydro-7a-methyl-1-[1-[5,5,5 trifluoro-4-hydroxy-4-(trifluoromethyl)-2-pentenyl] cyclopropyl]-4H-inden-4-one(0.8 g) as colorless crystals: mp 124–125° C.; [α$_D^{25}$-2.6° (EtOH, c=1.00); IR (CHCl$_3$) 3568, 1706 cm$^{-1}$; $^1$H NMR (CDCl$_3$) δ 0.15 (1 H, m), 0.36 (2 H, m), 0.60 (1 H, m), 0.65 (3 H, s), 1.15 (1 H, m), 1.50–1.80 (4 H, m), 1.85–2.3 (4 H, m), 2.45 (1 H, dd, J=7.6, 6.8 Hz), 2.91 (1 H, ddd, J=16,7.6, 5.9 Hz), 2.98 (1 H, s, OH), 5.42 (1 H, d, J=12 Hz), 6.10 (1 H, ddd, J=12, 7.6, 6.8 Hz). MS m/z 398 (M$^+$, 22). Anal. Calcd for C$_{19}$ $_{H24}$F$_6$O$_2$: C, 57.28; H, 6.07; F, 28.61. Found: C, 57.39; H, 6.01; F, 28.75.

Step 3

A solution of [1R-[1α(Z),3aβ,7aα]]octahydro-7a-methyl-1-[1-[5,5,5-trifluoro-4-hydroxy-4-(trifluoromethyl)-2-pentenyl]cyclopropyl]-4H-inden-4-one(0.75 g, 1.88 mmol) and 1-(trimethylsilyl)imidazole (2.6 ml, 17.75 mmol) in dichloromethane (20 ml) was stirred under argon for 7 hr and then diluted with water (10 ml). After stirring for 15 min., the reaction mixture was poured into dichloromethane (60 ml) and water (50 ml). The organic phase was collected and the aqueous phase was re-extracted with dichloromethane. The combined organic extracts were washed with water, dried over magnesium sulfate and evaporated to give 0.87 g of a partially crystalline solid. Purification by flash chromatography on a silica gel with 20% ethyl acetate in hexanes as eluant gave 0.83 g of colorless crystals. The crystals were dissolved in ether (5 ml), filtered through a 0.45 mm filter (Millex-HV) and the filtrate was diluted with hexane (5 ml). The ether was evaporated and the solution was left at -1° C. overnight. Filtration of the solid gave [1R-[1α(Z),3aβ,7aα]]octahydro-7a-methyl-1-[1-5,5,5-trifluoro-4-(trifluormethyl)-4-[(trimethylsilyl)oxy]-2-pentenyl]cyclopropyl]-4H-inden-4-one (0.80 g) as colorless crystals: mp 70–71° C.; [α]$_D^{25}$+0.9° (MeOH, c=1.00); IR (CHCl$_3$) 1706 cm$^{-1}$; $^1$H NMR (CDCl$_3$) δ 0.11 (1 H, m); 0.22 (9 H, s), 0.32 (2 H, m), 0.65 (1 H, m), 0.69 (3 H, s), 1.12 (1 H, m), 1.50–1.73 (4 H, m), (1.90–2.30 (7 H m), 2.4 (1 H, dd, J=17, 7 Hz), 2.94 (1 H, ddd, J=12, 7, 6 Hz), 5.41 (1H, d, J=12 Hz), 6.05 (1 H, ddd, J=12, 7, 6 Hz). MS m/z 471 (M$^+$+H, 100). Anal. Calcd for C$_{22}$H$_{32}$F6O$_2$Si: C, 56.15; H, 6.85; F, 24.22; Si, 5.97. Found: C, 56.26; H, 6.72; F, 24.29; Si, 5.80.

Example 8

1,25-Dihydroxy-23-(Z)-ene-26,27-hexafluoro-20,21, 28-cyclopropyl-cholecalciferol

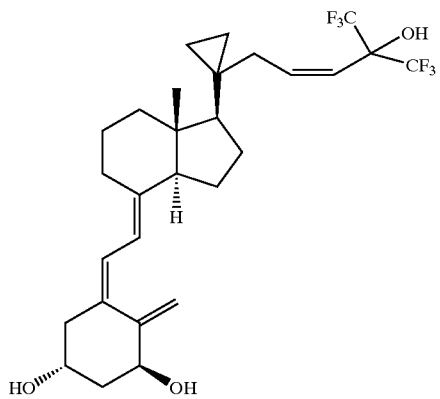

Step 1 n-Butyllithium (0.5 ml, 8 mmol, 1.6 M solution in hexanes) was added to a solution of [3S-(1Z,3α,5β)]-2-[3, 5-bis[[1,1-dimethylethyl)dimethylsilyl]oxy-2-methylenecyclohexylidene]ethyl]diphenylphosphine oxide (0.47 g, 0.8 mmol) in anhydrous tetrahydrofuran (4 ml) at –78° C. The resulting deep red solution was stirred at –78° C. for 7 minutes and then treated with a solution of [1R-1α ((Z),3aβ,7aα]]octahydro-7a-methyl-1-[1-[55,5,5-trifluoro-4-(trifluoromethyl)-4-[trimethylsily)oxy]-2-pentenyl] cyclopropyl]-4H-inden-4-one (0.19 g, 0.4 mmol) in anhydrous tetrahydrofuran (3 ml). After 2 h, the reaction mixture was allowed to warm to –10° C. and then quenched with a 1:1 mixture of 2 N Rochelle salt solution and 2 N potassium bicarbonate solution (5.0 ml). After 20 min., the reaction mixture was poured into a mixture of ethyl acetate (60 ml) and a 1:1 mixture of 2 N Rochelle salt solution and 2 N potassium bicarbonate solution (50 ml). The organic phase was collected and the aqueous phase was re-extracted with ethyl acetate. The combined organic extracts were washed with 50% brine (100 ml), dried over sodium sulfate and evaporated to give a gum. Purification by flash chromatography on a silica gel column with 20% ethyl acetate in hexanes as eluant gave 0.11 g of the trisilyl intermediate as colorless gum, which was without further purification in the next step.

Step 2

Tetrabutylammonium fluoride (3.0 ml, 3.0 mmol, 1.0 M solution in tetrahydrofuran) was added to a solution of the trisilyl intermediate (0.11 g) in tetrahydrofuran (3 ml) and the reaction mixture was stirred at room temperature. After 17 h, the reaction mixture was diluted with water (5 ml), stirred for additional 15 min., and then poured into a mixture of ethyl acetate (50 ml) and 50% brine (40 ml). The organic phase was collected and the aqueous phase was re-extracted with ethyl acetate. The combined organic extracts were washed with water, dried over sodium sulfate and evaporated to give 86 mg of a gum. Purification by flash chromatography on a silica gel column with ethyl acetate as eluant gave a gum, which was dissolved in anhydrous methyl formate (7 ml), filtered through a 0.4 μm filter, and evaporated to give 1,25-dihydroxy-23-(Z)-ene-26,27-hexafluoro-20,21,28-cyclopropyl-cholecalciferol (69 mg) as a colorless foam: $[\alpha]_D^{25}=-4.0°$ [MeOH, c=0.35); $\lambda_{max}$ (MeOH) 265 (ε15837), 211 (ε=14458) nm; IR (CHCl$_3$) 3598, 1651 cm$^{-1}$; $^1$H NMR (CDCl$_3$) δ 0.11(1 H, m), 0.29(2 H, m), 0.60 (3 H, s), 0.61(1 H, m), 1.10(1 H, m), 1.25–1.35 (1 H, m), 1.50 (6 H, m), 1.70 (2 H, m), 1.90 (2 H, m), 2.00 (3 H, m), 2.30 (2 h, m), 2.60 (1 H,d, J=12 Hz), 2.85 (2 H, m), 2.90 (1 H, s, OH), 4.22 (1 H, s), 4.42 (1 H, s), 4.99 (1 H, s), 5.32 (1 H, s), 5.42 (1 H, d, J=12 Hz), 5.99 (1 H, d=11 Hz), 6.10 (1 H, ddd, J=12,7,6), 6.36 (1 H,d, J=11 Hz); MS (FAB) m/z 535 (M$^+$+H).

Example 9

1,25-Dihydroxy-23-(Z)-ene-26,27-hexafluoro-20,21, 28-cyclopropyl-19-nor-cholecalciferol

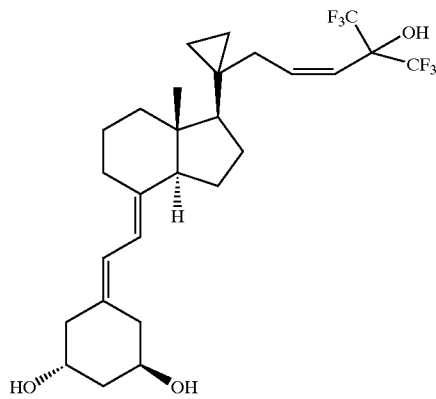

Step 1 n-Butyllithium (0.32 m, 0.5 mmol, 1.6 M solution in hexanes) was added to a solution of [3R-(3α,5β,Z)]-3,5-bis [[1,1-dimethylethyl)dimethyl-silyl]oxy]cyclohexylidene] ethyl]-diphenylphosphine oxide (0.285 g, 0.5 mmol) in anhydrous tetrahydrofuran (3 ml) at −78° C. The resulting deep red solution was stirred at −78° C. for 6 minutes and then treated with [1R-1α((Z),3aβ,7aα]]octahydro-7a-methyl-1-[1-[5,5,5-trifluoro-4-(trifluoromethyl)-4-[trimethylsilyl)oxy]-2-pentenyl]cyclopropyl]-4H-inden-4-one(0.12 g, 0.25 mmol) in anhydrous tetrahydrofuran (2 ml). After 3.0 h, the reaction mixture was allowed to warm to 15° C. and quenched with 1:1 mixture of 2 N Rochelle salt solution and 2 N potassium bicarbonate solution (5 ml). After 20 min., the reaction mixture was diluted with ethyl acetate (15 ml), poured into a mixture of ethyl acetate (50 ml) and a 1:1 mixture of 2 N Rochelle salt solution and 2 N potassium bicarbonate solution (50 ml). The organic phase was collected and the aqueous phase was re-extracted with ethyl acetate. The combined organic extracts were washed with 50% brine, dried over sodium sulfate and evaporated to give 0.58 g of a gum. Purification by flash chromatography on a silica gel column with 20% ethyl acetate in hexanes as eluant, gave 0.18 g of the trisilyl intermediate as a colorless gum, which was without further purification in the next step.

Step 2

Tetrabutylammonium fluoride (3.0 ml, 3.0 mmol, 1.0 M solution in tetrahydrofuran) was added to a solution of the trisilyl intermediate (0.18 g) in tetrahydrofuran (3 ml) and the reaction mixture was stirred at room temperature. After 42 h, the reaction mixture was diluted with water (5 ml), stirred for an additional 15 min., and then poured into a mixture of ethyl acetate (50 ml) and 50% brine (40 ml). The organic phase was collected and the aqueous phase was re-extracted with ethyl acetate. The combined organic extracts were washed with water, dried over sodium sulfate and evaporated to give 0.12 g of a gum. Purification by flash chromatography on a silica gel column with ethyl acetate as eluant gave a gum, which was dissolved in anhydrous methyl formate (8 ml), filtered through a 0.4 μm filter, and evaporated to give 1,25-dihydroxy-23-(Z)-ene-26,27-hexafluoro-20,21,28-cyclopropyl-19-nor-cholecalciferol (98 mg) as a colorless foam: $[\alpha]_D^{25}+47.4°$ [MeOH, c=0.35); $\lambda_{max}$ (MeOH) 260 (ε28200), 251 (ε=41760), 243 (ε=34747), 235 (sh, ε=23594) nm; IR (CHCl$_3$) 3603 cm$^{-1}$; $^1$H NMR (CDCl$_3$) δ 0.12 (1 H, m), 0.32 (2 H, m), 0.60 (3 H, s), 0.62 (1 H, m), 1.14 (1 H, m), 1.35 (1 H, m), 1.41(2 H m), 1.52 (4 H, m), 1.70 (2 H, m), 1.82 (1 H, m), 1.88–2.00 (2 H, m), 2.04 (2 H, m), 2.23 (3 H, m), 2.47 (1 H, d, J=12 Hz), 2.82 (3 H, m), 2.96(1 H, s, OH), 4.04 (1 H, s), 4.12 (1 H, s), 5.42 (1 H, d, J=12 Hz), 5.82 (1 H, d=11 Hz), 6.12 (1 H, ddd, J=12,7,6), 6.30 (1 H, d, J=11 Hz); MS (EI) m/z 522 (M$^+$, 60).

Example 10

1,25-Dihydroxy-20,21,28-cyclopropyl-cholecalciferol

Step 1

[1R-(1α,3aβ,4α,7aα)]-Octahydro-1-[1-(4-hydroxy-4-methylpentyl)cyclopropyl]-7a-methyl-4H-inden-4-ol A solution of 250 mg (0.86 mmol) of [1R-(1α,3aβ,4α, 7aα)]octahydro-1-[1-(4 hydroxy-4-methyl-2-pentynyl)-cyclopropyl]-7a-methyl-4H-inden-4-ol (Ro 27-3152) in 4.0 mL of ethyl acetate, 10 mL of hexane, 0.5 mL of ethanol, and 20 μL of quinoline was hydrogenated over 75 mg of Lindlar's catalyst (5% Pd+3.5% Pb on CaCO$_3$) at room temperature and atmospheric pressure for 2.5 hrs. The mixture was diluted with 50 mL of ethyl acetate and filtered over a pad of Celite, which was washed with 3×20 mL of ethyl acetate. The combined filtrate and washings were washed with 50 mL of 0.1 N HCl then 50 mL of water, dried (Na$_2$SO$_4$) and evaporated to give 244 mg of a colorless gum. Flash chromatography on 50 g of silica gel (40–65 μm; 3.5 cm diameter column) with 50% ethyl acetate, taking 12-mL fractions gave, after evaporation of fractions 10–18, 230 mg of a colorless gum. $^1$H NMR (CDCl$_3$) indicated it to be a mixture of the title compound and the 23,24 (Z)-ene product. The mixture was dissolved in 25 mL of CH$_2$Cl$_2$ and hydrogenated with 40 mg of [1,4-bis(diphenylphosphino) butane] (1,5-cyclooctadiene)-rhodium (1) tetrafluoroborate as catalyst in the presence of 1 drop of mercury in a Parr hydrogenator at room temperature and 50 psi for 3 hrs. After dilution with 30 mL of CH$_2$Cl$_2$, the mixture was filtered over a pad of Celite, which was washed with 3×40 mL of ethyl acetate. The filtrate and washings were evaporated to give an orange-colored gum, which was purified by flash chromatography on 45 g of silica gel (40–65 μm mesh; 3.5 cm diameter column) with 50% ethyl acetate in hexanes as eluent, taking 12-mL fractions. Fractions 13–17 were combined and evaporated to give a partially crystalline solid, which was triturated with hexane to give 204 mg of the title compound as colorless crystals, mp 126–128° C.; $[\alpha]_D^{25}+$42.6° (MeOH, c=0.3); IR 3611 cm$^{-1}$; $^1$H NMR (CDCl$_3$) δ −0.06 (1 H, m) 0.18 (2 H, m), 0.54 (1 H, m), 0.59 (1 H, m), (0.98 (3 H, m), 1.21 (6 H, s), 1.2–1.6 (15 H, m), 1.75–2.10

(5 H, m), 4.06 (1 H, s); MS (+FAB) m/z (295, M++1, 10). Anal. Calcd for $C_{19}H_{34}O_2$: C, 77.50; H, 11.64. Found C: 77.40; H, 11.89.

Step 2

[1R-(1α,3aβ,7aα)]-Octahydro-7a-methyl-1-[1-[5-methyl-5-[(trimethylsilyl)oxy]pentyl]cyclopropyl]-4H-inden-4-one To a stirred solution of 190 mg (0.64 mmol) of [1R-(1α,3aβ,4α,7aα)]-octahydro-1-[1-(4-hydroxy-4-methylpenyl)cyclopropyl]-7a-methyl-4H-inden-4-ol(Ro 27–5155) in 8.0 mL of $CH_2Cl_2$ was added 2.0 g (5.3 mmol) of pyridinium dichromate and the mixture was stirred at room temperature for 5.0 hrs. It was diluted with 20 mL of diisopropyl ether, stirred for 15 minutes and filtered over a pad of Celite, which was washed with 4×25 mL of diisopropyl ether. Evaporation of the filtrate and washings gave 184 mg of a pale yellow gum, which was purified by flash chromatography on 45 g of silica gel (40–65 μm mesh; 3.5 cm diameter column) with 45% of ethyl acetate on hexanes as eluent taking 12-mL fractions. Fractions 19–25 were combined and evaporated to give 158 mg of a colorless gum. The latter was dissolved in 5.0 mL of $CH_2Cl_2$ and treated with 1.0 mL (6.8 mmol) of 1-trimethylsilylimidazole and the mixture was stirred at room temperature for 2.0 hrs. It was diluted with 15 mL of water and 15 mL of $CH_2Cl_2$, stirred for a further 15 mins, and poured into a mixture of 40 mL of $CH_2Cl_2$ and 20 mL of 10% brine. The organic phase was separated and the aqueous phase was re-extracted with 3×50 mL of $CH_2Cl_2$. The combined organic extracts were washed with 3×60 mL of 10% brine, dried ($Na_2SO_4$) and evaporated to give 180 mg of a colorless gum, which was purified by flash chromatography on 45 g of silica gel (40–65 μm mesh; 3.5 cm diameter column) with 15% ethyl acetate in hexanes as eluent, taking 12-mL fractions. Fractions 10–14 were combined and evaporated to give 137 mg of a colorless gum, which was further purified by HPLC on silica gel (15–30 μm mesh; 50 mm×50 cm column; 70 mL/min) with 7.5% ethyl acetate in hexanes as eluent. The material eluting at 18.5 minutes was collected and evaporated to give 114 mg of the title compound as a gum, which solidified on keeping at 0° C. overnight; $[\alpha]_D^{25}$+7.8° (CHCl$_3$, c=0.41); IR 1707 cm$^{-1}$; $^1$H NMR (CDCl$_3$) δ 0.00 (1 H, m), 0.11 (9 H, s), 0.20 (2 H, m), 0.63 (2 H, m), 0.68 (3 H, s), 1.01 (1 H m), 1.21 (6 H, s), 1.30–1.72 (7 H, m), 1.90–2.10 (3 H, m), 2.15–2.23 (5 H, m), 2.5 (1 H, m); MS (+FAB) m/z 349.252 (M$^+$–15, 48).

Step 3

1,25-Dihydroxy-20,21,28-cyclopropyl-cholecalciferol

To a cooled (–78° C.), stirred solution of 335 mg (0.57 mmol) of [3S-(1Z,3α,5β)]-[2-[3,5-bis[(1,1-dimethylethyl)dimethylsilyl)oxy]-2-methylenecyclohexylidene]ethyl] diphenylphosphine oxide in 4.0 mL of anhydrous THF was added 0.35 mL (0.56 mmol) of a 1.6 M solution of n-butyllithium in hexanes and the resultant deep red solution was stirred at –78° C. for 7 minutes. A solution of 105 mg (0.28 mmol) of [1R-(1α,3aβ,7aα)]-octahydro-7a-methyl-1-[1-[5-methyl-5-[(trimethylsilyl)oxy]pentyl]cyclopropyl]-4-inden-4-one(Ro 27–5156) in 1.5 mL of anhydrous THF was added and the mixture was stirred at –78° C. for 3 hours and then at room temperature for 15 minutes. To the mixture was added 5 mL of a 1:1 mixture of 1.0 M Rochelle salt solution and 1.0 N KHCO$_3$ solution. After 15 minutes the mixture was poured into 50 mL of ethyl acetate and 40 mL of a 1:1 mixture of 1.0 M Rochelle salt solution and 1.0 N KHCO$_3$ solution. The organic phase was separated and the aqueous phase was re-extracted with 3×50 mL of ethyl acetate. The combined organic extracts were dried ($Na_2SO_4$) and evaporated to give 440 mg of a gum, which was chromatographed on 40 g of silica gel (40–65 μm mesh; 3.5 cm diameter column) with 5% ethyl acetate in hexanes as eluent, taking 12-mL fractions. Fractions 5–8 were combined and evaporated to give 131 mg of a colorless gum. The latter was dissolved in 3.0 mL of THF, treated with 1.5 mL (1.5 mmol) of a 1.0 M solution of tetra-n-butylammonium fluoride in THF, and stirred at room temperature for 17 hours. The mixture was diluted with 10 mL of water, stirred for 15 minutes, and poured into a mixture of 60 mL of ethyl acetate and 40 mL of 10% brine. The organic phase was separated and the aqueous phase was re-extracted with 3×60 mL of ethyl acetate. The combined organic extracts were washed with 4×100 mL of water, dried ($Na_2SO_4$), and evaporated to give 78 mg of a colorless gum, which was purified by flash chromatography on 40 g of silica gel (40–65 μm mesh; 3.2 cm diameter column) with ethyl acetate as eluent, taking 10-mL fractions. Fractions 10–12 were combined and evaporated to give a gum, which was dissolved in 10 mL of anhydrous methyl formate. The solution was filtered through a 0.4 μm filter and the filtrate was evaporated to give 64 mg of the title compound as a colorless foam: $[\alpha]_D^{25}$+18.30° (MeOH, c=0.18); IR (CHCl$_3$) 3608 cm$^{-1}$; $^1$H NMR (CDCl$_3$) δ 0.00 (2 H, m), 0.20 (2 H, m), 0.59 (3 H, s), 0.63 (2 H, m), 0.90 (2 H, m), 1.22 (6 H, s), 1.30–1.70 (20 H, m), 1.90–2.12 (5 H, m), 2.60 (1 H, d), 2.81 (1 H, d), 4.22 (1 H, br s), 4.43 (1 H, br s), 4.99 (1 H, s), 5.32 (1 H, s), 5.99 (1 H, d, J=11 Hz) 6.37 (1 H, d, J=11 Hz); MS (EI) Calcd. for $C_{28}H_{44}O_3$: m/z 428.3290. Found m/z 428.3297.

Example 11

Bone Anabolism in the Rat

The compounds of the present invention are more effective than 1,25-dihydroxy vitamin $D_3$ at bone accretion and do not induce hypercalciuria, nephrotoxicity, or hypercalcemia at therapeutically effective doses. This has been demonstrated as follows:

Three month old rats are ovariectomized (Ovx) and administered either 1,25-dihydroxy vitamin $D_3$ (vit. D in Table) or one of the compounds of the present invention once a day by mouth starting at 3 weeks post-ovariectomy and continuing until final sacrifice at 6 weeks postovariectomy. Control groups, both sham (rats that were not ovariectomized) and Ovx, received vehicle only. Blood and urine samples were collected twice, at 4 weeks post-ovariectomy and again at the 6 week mark and the amount of serum and urine calcium was determined. The final femoral calcium was determined upon sacrifice 6 weeks post-ovariectomy.

The bone mineral density of the right femur was determined by using a High Resolution Software Package on a QDR-1000W Bone Densitometer™ (Hologic, Walthan, Mass.). The animals were scanned by placing them on a scanning block in a supine position such that the right leg was perpendicular to the main body and the tibia was perpendicular to the femur. The increase in the bone mineral density and the amount of calcium in the urine and the serum for some of the compounds of this invention in this assay are given in the table below:

| CPD # see Table I | Surgery | Treatment | Dose μg/kg/day | Whole Femur BMD mg/cm² | Serum Calcium mg/dl (6th Week) | Urine Calcium/ Creatinine mg/dl (6th Week) |
|---|---|---|---|---|---|---|
| 3 | Sham | Vehicle | 0.000 | 0.2457 | 9.17 | 0.29 |
|   | Ovx | Vehicle | 0.000 | 0.2330 | 9.45 | 0.23 |
|   | Ovx | Vit D | 0.200 | 0.2368 | 10.65 | 1.71 |
|   | Ovx | Cpd #3 | 0.010 | 0.2396 | 10.25 | 0.83 |
| 4 | Sham | Vehicle | 0.000 | 0.2435 | 8.26 | 0.26 |
|   | Ovx | Vehicle | 0.000 | 0.2228 | 8.57 | 0.31 |
|   | Ovx | Vit D | 0.200 | 0.2349 | 9.49 | 1.37 |
|   | Ovx | Cpd #4 | 0.005 | 0.2413 | 8.94 | 0.60 |

Example 12

Cell Proliferation Assay in MCF-7 Breast Cancer Cells

MCF-7 cells are human mammary carcinoma cells that are positive for estrogen receptors. The potential activity of vitamin $D_3$ analogs against breast cancer was assessed from inhibition of proliferation of MCF-7 cells in culture.

MCF-7 cells were plated at 9000 cells/well in 24-well plates and incubated at 37° C. in 5% $CO_2$/95% air in Dulbecco's Modified Eagle Medium containing 10% fetal bovine serum, 700 nM insulin, 2 mM glutarnine, 0.1 mM MEM non-essential amino acids and 1 mM sodium pyruvate. Stock solutions of vitamin $D_3$ analogs were prepared at a concentration of 10 mM in absolute ethanol and stored at −20° C. under argon. Four days after plating, the number of MCF-7 were counted by removing the medium in 8 wells, rinsing the cells with 0.5 ml PBS without Ca/Mg and then incubating the cells with 0.3 ml of trypsin-EDTA. After 15 min., the trypsinization was stopped by adding 0.3 ml of medium. 0.2 ml aliquot was transferred from each well into dilu-vials containing 10 ml isoton and the number of cells were counted on Coulter Counter™ (Coulter, Miami, Fla.).

MCF-7 cells in the remaining wells were refed with either control medium or medium containing varying concentrations of the vitamin $D_3$ analog. After a further 7 days of culture, the number of MCF-7 cells in each well was assessed by removing the medium, rinsing the cells with 0.5 ml PBS without Ca/Mg and then incubating the cells with 0.5 ml of trypsin-EDTA for 15 min. The trypsinization was stopped by adding 0.5 ml of medium and 0.1 ml aliquot from each well was transferred into dilu-vials containing 10 ml isoton and the number of cells were counted on Coulter Counter™.

The anti-cell proliferation activities (expressed as $IC_{50}$, the concentration causing 50% reduction in MCF-7 cell growth in culture) of some compounds of the invention and 1,25-dihydroxy-cholecalciferol as a comparator, were:

| CPD # see Table 1 | $IC_{50}$ (nm) |
|---|---|
| 1,25-di(OH)-cholecalciferol | 149 |
| 1 | 0.50 |
| 2 | 0.30 |
| 3 | 0.03 |
| 4 | 0.05 |
| 5 | 0.03 |
| 6 | 0.03 |

The results of the above test show that compounds of this invention are more potent than 1,25-dihydroxy-cholecalciferol in inhibition of MCF-7 breast cells growth in culture.

Example 13

Cell Proliferation Assay in ZR-75 Breast Cancer Cells

ZR-75 cells are human mammary carcinoma cells that are positive for estrogen receptors. The potential activity of vitamin $D_3$ analogs against breast cancer was assessed from inhibition of proliferation of ZR-75 cells in culture.

ZR-75 cells were plated at 12,500 cells/well in 24-well plates and incubated at 37° C. in 5% $CO_2$/95% air in RPMI medium containing 10% fetal bovine serum and 2 mM L-glutamine. Stock solutions of vitamin $D_3$ analogs were prepared at a concentration of 10 mM in absolute ethanol and stored at −20° C. under argon. One day after plating, ZR-75 cells were refed with either control medium or medium containing varying concentrations of the vitamin $D_3$ analog. After a further 10 days of culture, the number of ZR-75 cells in each well was assessed from the reduction of the dye MTT (3-(4,5-dimethylthiazol-2-yl)-2,5 diphenyltetrazolium bromide), as described by F. Denizot and R. Lang, *J. Immunological Methods*, Vol. 89:271–277 (1986). MTT was added to each well to a final concentration of 1 mg/ml and the cells were incubated for a period of three hours, after which reduced MTT was extracted using 95% ethanol and the optical density was measured at a wavelength of 570 nm.

For each vitamin $D_3$ analog, the $IC_{50}$ value was determined from a graph relating the optical density of 570 nm to the concentration used.

The anti-cell proliferation activities (expressed as $IC_{50}$, the concentration of the vitamin $D_3$ analog corresponding to half-maximal reduction in 570 nm absorbance) of some compounds of the invention and 1,25-dihydroxy-cholecalciferol as a comparator, were:

| CPD # see Table 1 | $IC_{50}$ (nm) |
|---|---|
| 1,25-di(OH)-cholecalciferol | 13 |
| 2 | 0.90 |
| 3 | 0.01 |
| 4 | 0.15 |
| 5 | 0.10 |
| 6 | 0.10 |

The results of the above test show that compounds of this invention are more potent than 1,25-dihydroxy-cholecalciferol in inhibition of ZR-75 breast cells growth in culture.

Example 14

Effect of Vitamin $D_3$ Analogs on Secondary Hyperparathyroidism in the Rat Renal Insufficiency Model The parathyroid hormone suppressive activity of the vitamin $D_3$ analogs of this invention was demonstrated in rats with secondary hyperparathyroidism due to renal failure using the 7/8 nephrectomy induced rat model of renal failure (*Kidney International*, M. Fukugawa et al., 39:874–88 (1991).

Test Materials:
  compound formula (I)
  1,25$(OH)_2$ vitamin $D_3$ (control)
  Vehicle—Miglyol 812
  Female sprague Dawley rats were anesthetized, their right kidney removed and 2–3 branches of the left renal artery were ligated to achieve 7/8 nephrectomy. They were placed on a high phosphorous diet (0.06% Ca and 0.08 phosphorous). Approximately 3–6 weeks after surgery, rats were bled to screen serum PTH levels and rats with PTH levels between 100–500 pg/ml were selected for the study.

There was a pre-bleed (T=0) and each group was dosed daily for seven days by oral lavage with either the compound of Formula (I) (0.1 μg/kg/day), vehicle control or 1,25-(OH)$_2$ vitamin D$_3$ positive control. Compounds were pre-dissolved in ethanol and diluted with vehicle (Miglyol 812) followed by evaporation of the ethanol.

After the last day of dosing, the animals were bled again (T=1) and sacrificed. Serum PTH assays were done with Nichols Institute Diagnostic Kit #40-2240. Serum calcium assays were done with Sigma Diagnostic Kit #587 with o-cresophthalein. Serum creatinine assays were done with Sigma Diagnostic Kit #1600-320 with ammonium molybdate.

| CPD # see Table 1 | PTH pg/ml T=1-T=0 | Final Ca Levels (mg/ml) |
| --- | --- | --- |
| Vehicle | 145 | 9.04 |
| 1,25(OH)$_2$ vit. D$_3$ (0.1 μg/kg) | −18 | 9.75 |
| 3 (0.1 μg/kg) | −70 | 10.65 |
| 4 (0.1 μg/kg) | −137 | 10.08 |

The results show that the compounds of Formula (I) are more effective than 1,25(OH)$_2$ vit. D$_3$ in suppressing the elevated levels of parathyroid hormone.

Example 15

Oral Dosage Form Soft Gelatin Capsule

A capsule for oral administration is formulated under nitrogen in amber light from 0.01 to 25.0 mg of one of the compounds of the present invention in 150 mg of fractionated coconut oil, with 0.015 mg butylated hydroxytoluene (BHT) and 0.015 mg butylated hydroxyanisole (BHA), filled in a soft gelatin capsule.

The foregoing invention has been described in some detail by way of illustration and example, for the purposes of clarity and understanding. It will be obvious to one of ordinary skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, patent applications and publications cited in this application are hereby incorporated by reference in their entirety for all purposes to the same extent as if each individual patent, patent application or publication were so individually denoted.

We claim:

1. A compound selected from the group of compounds represented by Formula (I)

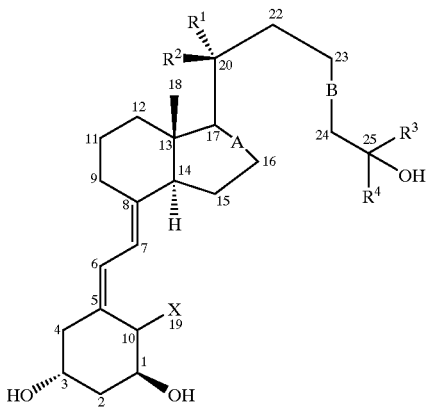

wherein
X is hydrogen or =CH$_2$;
R$^1$ and R$^2$ together with C20 form a (C$_3$–C$_6$)cycloalkyl or (C$_3$–C$_6$)cyclofluoroalkyl;
R$^3$ and R$^4$ are, independently of each other, a (C$_1$–C$_4$) alkyl or (C$_1$–C$_4$)fluoroalkyl, or R$^3$ and R$^4$ together with C25 form a (C$_3$–C$_6$)cycloalkyl or (C$_3$–C$_6$) cyclofluoroalkyl;
A is a single or a double bond; and
B is a triple bond.

2. The compound of claim 1, wherein:
B is a triple bond.

3. The compound of claim 2, wherein:
R$^1$ and R$^2$ together with C20 form a (C$_3$–C$_6$)cycloalkyl;
R$^3$ and R$^4$ are, independently of each other, a (C$_1$–C$_4$) alkyl or a (C$_1$–C$_4$)fluoroalkyl;
X is =CH$_2$; and
A is a single bond.

4. The compound of claim 3, wherein:
R$^1$ and R$^2$ together with C20 form a cyclopropyl group; and
R$^3$ and R$^4$ are, independently of each other, methyl, ethyl, trifluoromethyl, 1,1-difluoroethyl or 2,2,2-trifluoroethyl.

5. The compound of claim 4, wherein R$^3$ and R$^4$ are methyl namely, 1,25-dihydroxy-23-yne-20,21,28-cyclopropyl-cholecalciferol.

6. The compound of claim 4, wherein R$^3$ and R$^4$ are trifluoromethyl, namely 1,25-dihydroxy-23-yne-26,27-hexafluoro-20,21,28-cyclopropyl-cholecalciferol.

7. The compound of claim 2, wherein:
R$^1$ and R$^2$ together with C20 form a (C$_3$–C$_6$)cycloalkyl;
R$^3$ and R$^4$ are, independently of each other, a (C$_1$–C$_4$) alkyl or a (C$_1$–C$_4$)fluoroalkyl;
X is hydrogen; and
A is a single bond.

8. The compound of claim 7, wherein:
R$^1$ and R$^2$ together with C20 form a cyclopropyl group; and
R$^3$ and R$^4$ are, independently of each other, methyl, ethyl, trifluoromethyl, 1,1-difluoroethyl or 2,2,2-trifluoroethyl.

9. The compound of claim 8, wherein R$^3$ and R$^4$ are methyl, namely 1,25-dihydroxy-23-yne-20,21,28-cyclopropyl-19-nor-cholecaliferol.

10. The compound of claim 8, wherein R$^3$ and R$^4$ are trifluoromethyl, namely 1,25-dihydroxy-23-yne-26,27-hexafluoro-20,21,28-cyclopropyl-19-nor-cholecaliferol.

11. The compound of claim 2, wherein:
$R^1$ and $R^2$ together with C20 form a $(C_3-C_6)$cycloalkyl;
$R^3$ and $R^4$ are, independently of each other, a $(C_1-C_4)$ alkyl or a $(C_1-C_4)$fluoroalkyl;
X is =$CH_2$; and
A is a double bond.

12. The compound of claim 11, wherein:
$R^1$ and $R^2$ together with C20 form a cyclopropyl group; and
$R^3$ and $R^4$ are, independently of each other, methyl, ethyl, trifluoromethyl, 1,1-difluoroethyl or 2,2,2-trifluoroethyl.

13. The compound of claim 2, wherein:
$R^1$ and $R^2$ together with C20 form a $(C_3-C_6)$cycloalkyl;
$R^3$ and $R^4$ are, independently of each other, a $(C_1-C_4)$ alkyl or a $(C_1-C_4)$fluoroalkyl;
X is $H_2$; and
A is a double bond.

14. The compound of claim 13, wherein:
$R^1$ and $R^2$ together with C20 form a cyclopropyl group; and
$R^3$ and $R^4$ are, independently of each other, methyl, ethyl, trifluoromethyl, 1,1-difluoroethyl or 2,2,2-trifluoroethyl.

15. The compound of claim 1, wherein:
A is a double bond; and
B is a double bond.

16. The compound of claim 15, wherein:
$R^1$ and $R^2$ together with C20 form a $(C_3-C_6)$cycloalkyl;
$R^3$ and $R^4$ are, independently of each other, a $(C_1-C_4)$ alkyl or a $(C_1-C_4)$fluoroalkyl; and
X is =$CH_2$.

17. The compound of claim 16, wherein:
$R^1$ and $R^2$ together with C20 form a cyclopropyl group; and
$R^3$ and $R^4$ are, independently of each other, methyl, ethyl, trifluoromethyl, 11-difluoroethyl or 2,2,2-trifluoroethyl.

18. The compound of claim 15, wherein:
$R^1$ and $R^2$ together with C20 form a $(C_3-C_6)$cycloalkyl;
$R^3$ and $R^4$ are, independently of each other, a $(C_1-C_4)$ alkyl or a $(C_1-C_4)$fluoroalkyl; and
X is $H_2$.

19. The compound of claim 18, wherein:
$R^1$ and $R^2$ together with C20 form a cyclopropyl group; and
$R^3$ and $R^4$ are, independently of each other, methyl, ethyl, trifluoromethyl, 1,1-difluoroethyl or 2,2,2-trifluoroethyl.

20. The compound of claim 1, wherein:
A is a single bond; and
B is a cis double bond.

21. The compound of claim 20, wherein:
$R^1$ and $R^2$ together with C20 form a $(C_3-C_6)$cycloalkyl;
$R^3$ and $R^4$ are, independently of each other, a $(C_1-C_4)$ alkyl or a $(C_1-C_4)$fluoroalkyl; and
X is =$CH_2$.

22. The compound of claim 21, wherein:
$R^1$ and $R^2$ together with C20 form a cyclopropyl group; and
$R^3$ and $R^4$ are, independently of each other, methyl, ethyl, trifluoromethyl, 1,1-difluoroethyl or 2,2,2-trifluoroethyl.

23. The compound of claim 22, wherein $R^3$ and $R^4$ are trifluoromethyl namely, 1,25-dihydroxy-23-(Z)-ene-26,27-hexafluoro-20,21,28-cyclopropyl-cholecalciferol.

24. The compound of claim 20, wherein:
$R^1$ and $R^2$ together with C20 form a $(C_3-C_6)$cycloalkyl;
$R^3$ and $R^4$ are, independently of each other, a $(C_1-C_4)$ alkyl or a $(C_1-C_4)$fluoroalkyl; and
X is $H_2$.

25. The compound of claim 24, wherein:
$R^1$ and $R^2$ together with C20 form a cyclopropyl group; and
$R^3$ and $R^4$ are, independently of each other, methyl, ethyl, trifluoromethyl, 1,1-difluoroethyl or 2,2,2-trifluoroethyl.

26. The compound of claim 25, wherein $R^3$ and $R^4$ are trifluoromethyl namely, 1,25-dihydroxy-23-(Z)-ene-26,27-hexafluoro-20,21,28-cyclopropyl-19-nor-cholecalciferol.

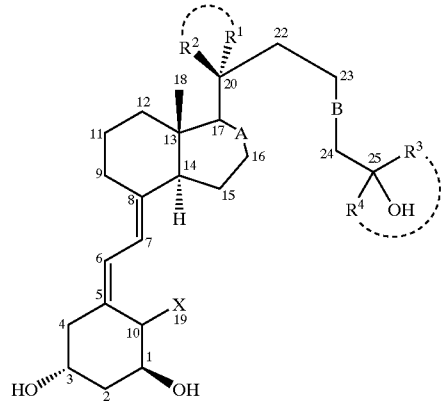

27. A method of treating osteoporosis via administration of a therapeutically effective amount of a compound of Formula (I)

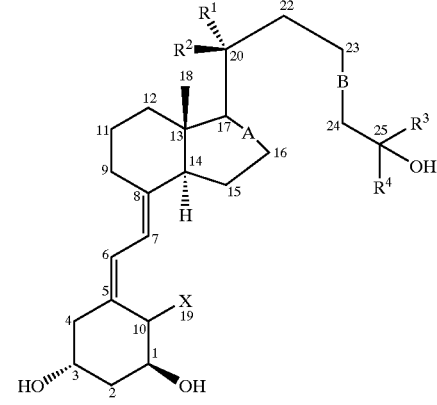

wherein
X is hydrogen or =$CH_2$;
$R^1$ and $R^2$ together with C20 form a $(C_3-C_6)$cycloalkyl or $(C_3-C_6)$cyclofluoroalkyl;
$R^3$ and $R^4$ are, independently of each other, a $(C_1-C_4)$ alkyl or $(C_1-C_4)$fluoroalkyl, or $R^3$ and $R^4$ together with C25 form a $(C_3-C_6)$cycloalkyl or $(C_3-C_6)$ cyclofluoroalkyl;
A is a single or a double bond; and
B is a triple bond;
or a prodrug thereof.

28. A method of treating leukemia, colon cancer, breast cancer or prostate cancer via administration of a therapeutically effective amount of a compound of Formula (I)

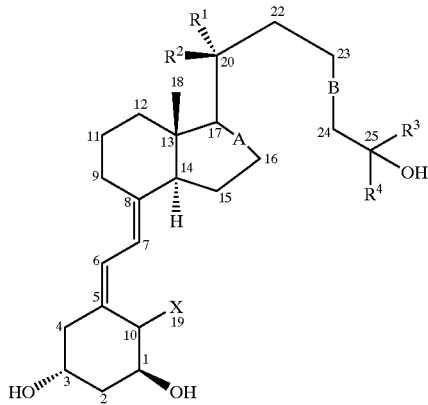

wherein
X is hydrogen or $=CH_2$;
$R^1$ and $R^2$ together with C20 form a $(C_3–C_6)$cycloalkyl or $(C_3–C_6)$cyclofluoroalkyl;
$R^3$ and $R^4$ are, independently of each other, a $(C_1–C_4)$ alkyl or $(C_1–C_4)$fluoroalkyl, or $R^3$ and $R^4$ together with C25 form a $(C_3–C_6)$cycloalkyl or $(C_3–C_6)$ cyclofluoroalkyl;
A is a single or a double bond; and
B is a triple bond;
or a prodrug thereof.

29. A method of treating secondary hyperparathyroidism via administration of a therapeutically effective amount of a compound of Formula (I)

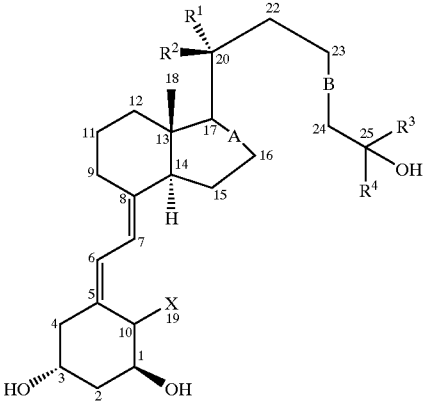

wherein
X is hydrogen or $=CH_2$;
$R^1$ and $R^2$ together with C20 form a $(C_3–C_6)$cycloalkyl or $(C_3–C_6)$cyclofluoroalkyl;
$R^3$ and $R^4$ are, independently of each other, a $(C_1–C_4)$ alkyl or $(C_1–4)$fluoroalkyl, or $R^3$ and $R^4$ together with C25 form a $(C_3–C_6)$cycloalkyl or $(C_3–C_6)$ cyclofluoroalkyl;
A is a single or a double bond; and
B is a triple bond;
or a prodrug thereof.

30. A pharmaceutical composition comprising an effective amount of a compound of claim 1.

* * * * *